(12) United States Patent
Lyte

(10) Patent No.: US 10,696,942 B2
(45) Date of Patent: Jun. 30, 2020

(54) MEDIA COMPOSITIONS FOR PROMOTING BACTERIAL AND FUNGAL GROWTH

(71) Applicant: Texas Tech University System, Lubbock, TX (US)

(72) Inventor: Mark Lyte, Ames, IA (US)

(73) Assignee: Texas Tech University System, Lubbock, TX (US)

( * ) Notice: Subject to any disclaimer, the term of this patent is extended or adjusted under 35 U.S.C. 154(b) by 210 days.

(21) Appl. No.: 15/820,637

(22) Filed: Nov. 22, 2017

(65) Prior Publication Data

US 2018/0094234 A1 Apr. 5, 2018

Related U.S. Application Data

(62) Division of application No. 14/355,890, filed as application No. PCT/US2012/063246 on Nov. 2, 2012, now abandoned.

(60) Provisional application No. 61/554,813, filed on Nov. 2, 2011.

(51) Int. Cl.
*C12N 1/20* (2006.01)
*C12N 1/38* (2006.01)
*C12N 1/14* (2006.01)
*C12N 1/16* (2006.01)
*C12Q 1/02* (2006.01)

(52) U.S. Cl.
CPC .......... *C12N 1/20* (2013.01); *C12N 1/14* (2013.01); *C12N 1/16* (2013.01); *C12N 1/38* (2013.01); *C12Q 1/025* (2013.01); *C12N 2500/30* (2013.01); *C12N 2500/34* (2013.01); *C12N 2500/36* (2013.01); *C12N 2500/38* (2013.01)

(58) Field of Classification Search
CPC ... C12N 1/14; C12N 1/16; C12N 1/20; C12N 1/38; C12N 2500/30; C12N 2500/34; C12N 2500/361; C12N 2500/38; C12Q 1/025
See application file for complete search history.

(56) References Cited

U.S. PATENT DOCUMENTS

| | | |
|---|---|---|
| 6,617,126 B1 | 9/2003 | Horn |
| 8,240,482 B2 * | 8/2012 | Lescoche .............. B01D 61/12 210/189 |
| 2009/0087517 A1 | 4/2009 | Freestone et al. |
| 2009/0324761 A1 | 12/2009 | Khoo et al. |
| 2011/0206786 A1 * | 8/2011 | West .................. A61K 31/7048 424/727 |
| 2011/0268825 A1 * | 11/2011 | Burgos .................. A23L 33/105 424/732 |
| 2014/0314889 A1 | 10/2014 | Duttaroy |

FOREIGN PATENT DOCUMENTS

CN 101406683 A 4/2009
WO 2007052081 A2 5/2007

OTHER PUBLICATIONS

Chan-Blanco, Y. et al., "Using banana to generate lactic acid through batch process fermentation," Appl Microbiol Biotechnol (2003) 63:147-152.
Extended European Search Report [EP 12845470.9] dated May 21, 2015.
International Search Report [Australia Search Authority] PCT/US2012/063246 dated Jan. 3, 2013.
Jiraratananon, J. et al., "A study of fouling in the ultrafiltration of passion fruit juice," Journal of Membrane Science 111 (1996) 39-48.
Lyte, Mark "Induction of Gram-negative bacterial growth by neurochemical containing banana (*Musa x patadisiaca*) extracts" FEM Microbiology Letter 154 (1997) 245-250.
Sims, Charles A. et al., "Color, Polyphenoloxidase, and Sensory Changes in Banana Juice as Affected by Heat and Ultrafiltration," Journal of Food Quality 17 (1994) 371-379.
Sutherland, Juliet et al., "In vitro effects of food extracts on selected probiotic and pathogenic bacteria," International Journal of Food Sciences and Nutrition, Dec. 2009; 60(8): 717-727.
Tanada-Palmu, Patricia et al., "Production of a banana (*Musa cavendishii*) extract containing no polyphenol oxidase by ultrafiltration," Journal of the Science of Food and Agriculture 79:643-647 (1999).

* cited by examiner

*Primary Examiner* — Susan M Hanley
(74) *Attorney, Agent, or Firm* — Edwin S. Flores; Daniel J. Chalker; Chalker Flores, LLP

(57) ABSTRACT

Methods and compositions for enhancing or promoting germination of bacterial spores, and yeasts are disclosed herein. The composition of the present invention comprises an extract obtained from banana or any member belonging to the genus *Musa* that may be used alone or in a growth medium to promote and enhance germination of bacterial spores, growth of bacterial, yeast, and fungal cell cultures.

7 Claims, 7 Drawing Sheets

MEDIA COMPOSITIONS FOR PROMOTING BACTERIAL AND FUNGAL GROWTH

CROSS-REFERENCE TO RELATED APPLICATIONS

This application is a Divisional of co-pending U.S. patent application Ser. No. 14/355,890 filed May 2, 2014, now abandoned, which is a U.S. National Stage of International Application No. PCT/US2012/063246 filed on Nov. 2, 2012 and claims the priority of U.S. Provisional Patent Application Ser. No. 61/554,813, filed on Nov. 2, 2011, the contents of which are incorporated by reference herein in their entirety.

TECHNICAL FIELD OF THE INVENTION

The present invention relates in general to the field of media for promoting growth of bacteria and yeasts, and more particularly, to the preparation of a media from fruits to promote bacterial and fungal growth.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in compositions for promoting for enhancing growth of microorganisms in vitro.

U.S. Patent Application Publication No. 2009/0087517 (Freestone et al. 2009) discloses the production and use of an extract obtained from *Musa* spp., preferably from bananas, in the promotion of growth of Gram-positive bacteria such as lactic acid bacteria. The extract is also useful for growth enhancement of environmentally-stressed Gram negative bacteria. Fermented foods containing such extracts are also described.

U.S. Pat. No. 6,617,126 issued to Horn (2003) relates to a method for improving the growth and detection of bacteria, yeasts, fungi or cocci, by adding sterile-filtered yeast extract and/or p-iodonitrotetrazolium violet to the culture medium. The method of the Horn patent is especially suited for the detection of mycobacteria or germs under stress conditions, such as airborne germs after the stress of desiccation in the air.

Others, such as Chan-Blanco, et al., in their publication "Using banana to generate lactic acid through batch process fermentation", APPL MICROBIOL BIOTECHNOL (2003) 63:147-152, have used waste banana for generating lactic acid through batch fermentation, using *Lactobacillus casei* under three treatments. Two treatments consisted of substrates of diluted banana puree, one of which was enriched with salts and amino acids. When fermentation was evaluated over time and significant differences were found in the three treatments for each of five variables analyzed (generation and productivity of lactic acid, and consumption of glucose, fructose, and sucrose). The skilled artisan will recognize that fermentation is a biochemical process that is not dependent on cell growth or division. Furthermore, the reference found a decrease in the growth of bacteria when exposed to a banana extract. Despite the teachings in the art, there remains a need in the art for a potent media and media supplements that can be used to grow in a vigorous and consistent manner a wide variety of organisms for commercial and other application.

SUMMARY OF THE INVENTION

The present invention discloses compositions and methods for preparing extracts from plants, for example, the plant family Musaceae (genera *Musa*) to promote or enhance bacterial and fungal growth by itself or as components of a growth medium. The present invention may be used with a variety of fruits and plants processed as described herein.

In one embodiment the present invention includes compositions and methods of preparing a plant extract comprising the steps of: combining a fruit core from a flowering plant, wherein the fruit core is substantially free of: the fruit peel, the fruit ends, and any discoloration, bruises, microbial growth, environmental stress, or any combinations thereof with distilled water; blending the fruit and distilled water in a processor to form a smooth mixture; separating the blended fruit and distilled water into a supernatant and a sediment, wherein the sediment is discarded and the supernatant is further processed; sterilizing the supernatant; optionally performing a second separation on the sterilized supernatant to remove any separated sediment or debris; and clarifying the sterilized supernatant by one or more techniques, wherein the clarification results in an isolation of a fraction of the supernatant of a desired molecular weight range comprising one or more active components responsible for the promotion or enhancement of germination, growth, viability, yield, metabolite production, or any combinations thereof of the one or more microorganisms grown in a media comprising the filtered supernatant.

The present invention provides a spray dried composition for promoting or enhancing germination, growth, viability, yield, metabolite production, or any combinations thereof of one or more microorganisms having a spray dried extract obtained from one or more flowering plants, made by a method comprising: combining a fruit core from a flowering plant, wherein the fruit core is substantially free of: the fruit peel, the fruit ends, and any discoloration, bruises, microbial growth, environmental stress, or any combinations thereof with distilled water; blending the fruit and distilled water in a processor to form a smooth mixture; separating the blended fruit and distilled water into a supernatant and a sediment, wherein the sediment is discarded and the supernatant is further processed; sterilizing the supernatant; optionally performing a second separation on the sterilized supernatant to remove any separated sediment or debris; and filtering the sterilized supernatant by a flat sheet or hollow fiber membrane filtration process, wherein the membrane filtration results in an isolation of a fraction of the supernatant of a desired molecular weight range comprising one or more active components responsible for the promotion or enhancement of germination, growth, viability, yield, metabolite production, or any combinations thereof of the one or more microorganisms grown in a media comprising the filtered supernatant. The spray dried extract may be made into a powder and/or used as a powder or dissolved into a mixture or solution.

The composition may be encapsulated in the form of a bead, a coating, a capsule, a pill or combination thereof. In addition the composition may include multiple layers combined to form a single composition, e.g., the composition and probiotic encapsulated in a bead which is then coated with a first release modifying coating that is coated with a probiotic that is again coated with a release modifying coating that is similar or different to the first release modifying coating. The encapsulation material and release modifying coating may be a water-permeable material, diffusion barrier coating material, polymeric coating material or a combination thereof and form an extended release coating, a controlled release coating, a delayed release coating, an immediate release coating or a combination thereof. the composition may also include one or more probiotics are selected from *B. subtilis*, *B. subtilis spores*, Poaceae, Fabaceae, Musaceae, Solanaceae, Cucurbitaceae, Brassicaceae, Apiaceae, Rutaceae, Rosaceae, *Lactobacillus rhamnosus* GG, *Bifidobacterium* species, *Bifidobacterium longum*, *Bifidobacterium animalis* subsp. *lactis* BB-12, *Saccharomyces*, moulds, *Aspergillus, Lactobacillus, Bifidobacterium, Streptococcus, Enterococcus, Lactobacillus johnsonii, Bifidobacterium lactis, Streptococcus thermophilus, Lactobacillus paracasei, Lactobacillus, Streptococcus, Bifidobacterium, Bacteroides, Clostridium, Fusobacterium, Nelissococcus, Propionibacterium, Enterococcus, Lactococcus, Staphylococcus, Peptostreptococcus, Bacillus, Pediococcus, Micrococcus, Leuconostoc, Weissella, Aerococcus, Oenococcus, Enterococcccus, Clostridium, Escherichia, Klebsiella, Campylobacter, Peptococcus, Heliobacter, Hemophylus, Staphylococcus, Yersinia, Vibrio, Shigella, Salmonella, Streptococcus, Proteus, Pseudomonas, Toxoplasmosis*, and *Rotavirus* species or spores thereof.

The present invention provides an encapsulated composition for promoting or enhancing germination, growth, viability, yield, metabolite production, or any combinations thereof of one or more microorganisms comprising one or more probiotics and one or more extracts obtained from one or more flowering plants encapsulated by an encapsulation material, wherein the one or more extracts obtained from one or more flowering plants, made by a method comprising:

combining a fruit core from a flowering plant, wherein the fruit core is substantially free of: the fruit peel, the fruit ends, and any discoloration, bruises, microbial growth, environmental stress, or any combinations thereof with distilled water; blending the fruit and distilled water in a processor to form a smooth mixture; separating the blended fruit and distilled water into a supernatant and a sediment, wherein the sediment is discarded and the supernatant is further processed; sterilizing the supernatant; optionally performing a second separation on the sterilized supernatant to remove any separated sediment or debris; and filtering the sterilized supernatant by a flat sheet or hollow fiber membrane filtration process, wherein the membrane filtration results in an isolation of a fraction of the supernatant of a desired molecular weight range comprising one or more active components responsible for the promotion or enhancement of germination, growth, viability, yield, metabolite production, or any combinations thereof of the one or more microorganisms grown in a media comprising the filtered supernatant.

In one aspect, the method further comprises the optional steps of: processing the extract with the one or more active components by one or more techniques selected from lyophilization, vacuum centrifugation, spray drying, or any combinations thereof; and performing one or more analytical tests or chemical analysis tests on the plant extract, wherein at least one of the test is selected from the group consisting of sugar profile, moisture content, vitamin A analysis, crude protein estimation, complete mineral analysis, non-protein nitrogen (NPN) equivalent to protein, Brix index, specific gravity, vitamin C, crude fiber analysis, pH, fatty acid composition by gas chromatography (GC), and any combinations thereof. In another aspect, the clarification is achieved by a flat sheet or hollow fiber membrane, tubular membrane, spiral wound, hollow fiber, pressurized, immersed, or ceramic filtration process. In another aspect, the fraction comprising the active components comprises one or more active components in the molecular weight range of 250-1,000 or even 500-1,000 Daltons. In another aspect, the microorganisms comprise bacteria, yeasts, fungi, or any combinations thereof. In another aspect, the microorganisms comprise bacteria selected from gram positive bacteria, gram negative bacteria, lactic acid bacteria, aerobic bacteria, anaerobic bacteria, or any combinations thereof. In another aspect, the microorganisms comprise a bacteria selected from one or more bacteria belonging to a genus *Bacillus* selected from the group consisting of *Bacillus thuringiensis, Bacillus coagulans, Bacillus subtilis, Bacillus amyloliquefaciens, Bacillus licheniformis*, and any combinations thereof. In another aspect, the composition is added to a growth, sporulation, or a fermentation medium to promote or enhance spore germination, growth, viability, yield, metabolite production, or any combinations thereof of the one or more microorganisms, wherein the growth medium comprises nutrient broth (NB), nutrient agar (NA), Luria-Bertani broth (LB), Mueller-Hinton cation-adjusted broth (MH), a sporulation broth, eosin-methylene blue agar (EMB), yeast and mold (YM), blood agar, MacConkey agar, Hektoen enteric agar (HE), mannitol salt agar (MSA), Terrific Broth (TB), xylose lysine deoxycholate (XLD), RPMI-1640 media, molasses-based media (e.g., beet and cane molasses), buffered charcoal yeast extract agar, minimal media, or any combinations or modifications thereof. In another aspect, the composition is added to the growth medium at a concentration ranging from 0.01%-15%, 0.5%-10%, or 1%-5%. In another aspect, the flowering plant is selected from a plant belonging to a family selected from the group consisting of Poaceae, Fabaceae, Musaceae, Solanaceae, Cucurbitaceae, Brassicaceae, Apiaceae, Rutaceae, Rosaceae, and any combinations thereof. In another aspect, the inoculum of microorganisms is sub-optimal. In another aspect, the fruit is ripened and then frozen prior to processing.

Another embodiment of the invention includes a method for promoting or enhancing germination, growth, viability, yield, metabolite production, or any combinations thereof of one or more microorganisms comprising the step of: providing a fermentation or growth medium for a cultivation or growth of the one or more microorganisms; adding an inoculum or spores of the one or more microorganisms in need of a promotion or enhancement of germination, growth, viability, yield, metabolite production, or any combinations thereof, wherein the inoculum comprises the one or more microorganisms in a lag phase or an exponential phase of a microbial growth cycle; and adding a plant extract obtained from one or species belonging to the family Musaceae to the growth medium or the inoculum, wherein the plant extract may be added to the growth medium prior to the addition of the inoculum or the spores, or periodically during an exponential or a stationary phase of the microbial growth cycle. In one aspect, the method further comprises the steps of: monitoring the growth of the one or more microorganisms through the phases of the microbial growth cycle; and harvesting the one or more microorganisms when a desired growth, viability, or yield is achieved, a desired level of metabolite production is reached, a death phase of the microbial growth cycle is reached, or any combinations thereof. In another aspect, the microorganisms comprise bacteria, yeasts, fungi, or any combinations thereof. In another aspect, the microorganisms comprise bacteria selected from gram positive bacteria, gram negative bacteria, lactic acid bacteria, aerobic bacteria, anaerobic bacteria, or any combinations thereof. In another aspect, the microorganisms comprise bacteria selected from one or more bacteria belonging to a genus Bacillus selected from the group consisting of Bacillus thuringiensis, Bacillus coagulans, Bacillus subtilis, Bacillus amyloliquefaciens, Bacillus licheniformis, and any combinations thereof. In another aspect, the growth medium comprises nutrient broth (NB), nutrient agar (NA), Luria-Bertani broth (LB), Mueller-Hinton cation-adjusted broth (MH), a sporulation broth, eosin-methylene blue agar (EMB), yeast and mold (YM), blood agar, MacConkey agar, Hektoen enteric agar (HE), mannitol salt agar (MSA), Terrific Broth (TB), xylose lysine deoxycholate (XLD), RPMI-1640 media, minimally-based media, molasses-based media, buffered charcoal yeast extract agar, or any combinations or modifications thereof. In another aspect, the extract is added to the growth medium at a concentration ranging from, e.g., 0.01-15%, 0.1-10%, 0.5-5% 0.1%-15% volume to volume. In certain aspects, it is added at 0.01, 0.05, 0.1, 0.2, 0.3, 0.4, 0.5, 0.6, 0.7, 0.8, 0.9, 1.0, 1.5, 2.0, 2.5, 5.0, 7.5, 8, 9, 10, 11, 12, 13, 14 or 15%. In another aspect, the extract is obtained from one or more fruits of the plant belonging to the family Musaceae, wherein the fruit comprises bananas, plantains, Ensete, Musella, and any combinations thereof. In another aspect, the extract is made from one or more bananas or plantains by a method comprising the steps of: blending the bananas or plantains with distilled water in a processor to form a smooth mixture; centrifuging the mixture to separate a supernatant and a sediment, wherein the sediment is discarded and the supernatant is taken for further processing; sterilizing the supernatant; performing a second centrifugation if necessary on the sterilized supernatant to remove any separated sediment or debris; and purifying the sterilized supernatant by a membrane filtration process, wherein the membrane filtration results in an isolation of a fraction of the supernatant of a desired molecular weight range comprising one or more active components responsible for the promotion or enhancement of the germination, the growth, the viability, the yield, the metabolite production, or any combinations thereof of the one or more microorganisms. In another aspect, the method further comprises the optional step of processing the extract with the one or more active components by one or more techniques selected from lyophilization, vacuum centrifugation, spray drying, or any combinations thereof. In another aspect, the fraction comprising the active components comprises one or more active components in the molecular weight range of 250 to 100 or even 500-1,000 Daltons. In another aspect, the membrane filtration process is performed using a flat-sheet or a hollow fiber membrane, tubular membrane, spiral wound, hollow fiber, pressurized, immersed, or ceramic filtration system. In another aspect, the inoculum of microorganisms is suboptimal. In another aspect, the fruit is ripened and then frozen prior to processing. In another aspect, in the step prior to blending the bananas, the bananas are frozen and thawed and then batch processed.

In yet another embodiment, the present invention includes method of preparing a plant extract from one or more bananas or plantains for promoting or enhancing germination, growth, viability, yield, metabolite production, or any combinations thereof of one or more microorganisms comprising the steps of: providing one or more bananas or plantains; preparing the bananas or plantains for processing by a method comprising the steps of: inspecting the bananas or plantains for any portions showing discoloration, bruises, microbial growth, environmental stress, or any combinations thereof; cutting and discarding any portion of the bananas or plantains showing discoloration, bruises, microbial growth, environmental stress, or any combinations thereof; cutting and discarding the ends of the bananas or plantains; and placing the bananas or plantains in a blender or a processor along with distilled water; blending the bananas or plantains with the distilled water in a processor to form a smooth mixture; centrifuging the mixture to separate a supernatant and a sediment, wherein the sediment is discarded and the supernatant is taken for further processing; sterilizing the supernatant; performing a second centrifugation if necessary on the sterilized supernatant to remove any separated sediment or debris; and purifying the sterilized supernatant by a flat sheet or hollow fiber membrane filtration process, wherein the membrane filtration results in an isolation of a fraction of the supernatant of a desired molecular weight range comprising one or more active components responsible for the promotion or enhancement of the germination, the growth, the viability, the yield, the metabolite production, or any combinations thereof of the one or more microorganisms. In one aspect, the method further comprises the optional steps of: processing the extract with the one or more active components by one or more techniques selected from lyophilization, vacuum centrifugation, spray drying, or any combinations thereof; and performing one or more analytical tests or chemical analysis tests on the plant extract, wherein at least one of the test is selected from the group consisting of sugar profile, moisture content, vitamin A analysis, crude protein estimation, complete mineral analysis, non-protein nitrogen (NPN) equivalent to protein, Brix index, specific gravity, vitamin C, crude fiber analysis, pH, fatty acid composition by GC, and any combinations thereof. In one aspect, the fraction comprising the active components comprises one or more active components in the molecular weight range of 250-1,000 Daltons. In another aspect, the microorganisms comprise one or more bacteria, yeasts, or both. In another aspect, the microorganisms comprise a bacteria selected from one or more bacteria belonging to a genus Bacillus selected from the group consisting of Bacillus thuringiensis, Bacillus coagulans, Bacillus subtilis, Bacillus amyloliquefaciens, Bacillus licheniformis, and any combinations thereof. In another aspect, the composition is added to a growth, sporulation, or a fermentation medium to promote or enhance spore germination, growth, viability, yield, metabolite production, or any combinations thereof of the one or more microorganisms, wherein the growth medium comprises nutrient broth (NB), nutrient agar (NA), Luria-Bertani broth (LB), Mueller-Hinton cation-adjusted broth (MH), a sporulation broth, RPMI-1640 media, molasses-based media, or any combinations or modifications thereof. In another aspect, the extract is added to the growth medium at a concentration ranging from 0.01%-15%, 0.5%-10%, or 1%-5%. In another aspect, the fruit is ripened and then frozen prior to processing. In another aspect, the membrane filtration process is performed using a flat-sheet or a hollow fiber membrane, tubular membrane, spiral wound, hollow fiber, pressurized, immersed, or ceramic filtration.

Yet another embodiment of the present invention includes a method for promoting or enhancing germination, growth, viability, yield, metabolite production, or any combinations thereof of one or more Bacillus bacteria, yeast, or both comprising the steps of: providing a fermentation or growth medium for a cultivation or growth of the one or more

*Bacillus* bacteria, yeast, or both; adding an inoculum or spores of the one or more *Bacillus* bacteria, yeast, or both in need of a promotion or enhancement of germination, growth, viability, yield, metabolite production, or any combinations thereof, wherein the inoculum comprises the one or more microorganisms in a lag phase or an exponential phase of a microbial growth cycle; and adding an extract obtained from one or more bananas or plantains to the growth medium or the inoculum, wherein the extract may be added to the growth medium prior to the addition of the inoculum or the spores, or periodically during an exponential or a stationary phase of the microbial growth cycle. In one aspect, the method further comprises the steps of: monitoring the fermentation or the growth of the one or more *Bacillus* species bacteria, yeast, or both through the phases of the microbial growth cycle; and harvesting the one or more *Bacillus* species bacteria, yeast, or both when a desired growth, viability, or yield is achieved, a desired level of metabolite production is reached, a death phase of the microbial growth cycle is reached, or any combinations thereof. In another aspect, the *Bacillus* bacteria comprise one or more bacteria belonging to a genus *Bacillus* selected from the group consisting of *Bacillus thuringiensis, Bacillus coagulans, Bacillus subtilis, Bacillus amyloliquefaciens, Bacillus licheniformis*, and any combinations thereof. In another aspect, the growth medium comprises nutrient broth (NB), nutrient agar (NA), Luria-Bertani broth (LB), Mueller-Hinton cation-adjusted broth (MH), a sporulation broth, RPMI-1640 media, molasses-based media, or any combinations or modifications thereof. In another aspect, the extract is added to the growth medium at a concentration ranging from 0.01%-15%, 0.5%-10%, or 1%-5%. In another aspect, the extract from the one or more bananas or plantains is prepared by a method comprising the steps of: providing one or more bananas or plantains; preparing the bananas or plantains for processing by a method comprising the steps of: inspecting the bananas or plantains for any portions showing discoloration, bruises, microbial growth, environmental stress, or any combinations thereof; cutting and discarding any portion of the bananas or plantains showing discoloration, bruises, microbial growth, environmental stress, or any combinations thereof; cutting and discarding the ends of the bananas or plantains; and placing the bananas or plantains in a blender or a processor along with distilled water; blending the bananas or plantains with the distilled water in a processor to form a smooth mixture; centrifuging the mixture to separate a supernatant and a sediment, wherein the sediment is discarded and the supernatant is taken for further processing; sterilizing the supernatant; performing a second centrifugation if necessary on the sterilized supernatant to remove any separated sediment or debris; and purifying the sterilized supernatant by an ultrafiltration process that results in the isolation of a fraction of the supernatant of a desired molecular weight range comprising one or more active components responsible for the promotion or enhancement of the germination, the growth, the viability, the yield, the metabolite production, or any combinations thereof of the one or more microorganisms. In one aspect, the method further comprises the optional steps of: processing the extract with the one or more active components by one or more techniques selected from lyophilization, vacuum centrifugation, spray drying, or any combinations thereof; and performing one or more analytical tests or chemical analysis tests on the plant extract, wherein the tests comprise sugar profile, moisture content, vitamin A analysis, crude protein estimation, complete mineral analysis, non-protein nitrogen (NPN) equivalent to protein, Brix index, specific gravity, vitamin C, crude fiber analysis, pH, fatty acid composition by GC, or any combinations thereof. In another aspect, the fraction comprises the active components comprises one or more active components in the molecular weight range of 250-1,000 Daltons. In another aspect, the banana is ripened and then frozen prior to processing.

Yet another embodiment of the present invention includes a composition for promoting or enhancing germination, growth, viability, yield, metabolite production, or any combinations thereof of one or more microorganisms comprising an extract obtained from one or more flowering plants, made by a method comprising: combining a fruit core from a flowering plant, wherein the fruit core is substantially free of: the fruit peel, the fruit ends, and any discoloration, bruises, microbial growth, environmental stress, or any combinations thereof with distilled water; blending the fruit and distilled water in a processor to form a smooth mixture; separating the blended fruit and distilled water into a supernatant and a sediment, wherein the sediment is discarded and the supernatant is further processed; sterilizing the supernatant; optionally performing a second separation on the sterilized supernatant to remove any separated sediment or debris; and filtering the sterilized supernatant by a flat sheet or hollow fiber membrane filtration process, wherein the membrane filtration results in an isolation of a fraction of the supernatant of a desired molecular weight range comprising one or more active components responsible for the promotion or enhancement of germination, growth, viability, yield, metabolite production, or any combinations thereof of the one or more microorganisms grown in a media comprising the filtered supernatant. In one aspect, the flowering plant is selected from a plant belonging to a family selected from the group consisting of Poaceae, Fabaceae, Musaceae, Solanaceae, Cucurbitaceae, Brassicaceae, Apiaceae, Rutaceae, Rosaceae, and any combinations thereof. In another aspect, the flowering plant is a plant belonging to the family Musaceae. In another aspect, the extract is obtained from a fruit of the flowering plant of the family Musaceae, wherein the fruit is selected from bananas, plantains, Ensete, Musella, and any combinations thereof. In another aspect, the microorganisms comprise bacteria, yeasts, fungi, or any combinations thereof. In another aspect, the microorganisms comprise a bacteria selected from gram positive bacteria, gram negative bacteria, lactic acid bacteria, aerobic bacteria, anaerobic bacteria, or any combinations thereof. In another aspect, the microorganisms comprise a bacteria selected from one or more bacteria belonging to a genus *Bacillus* selected from the group consisting of *Bacillus thuringiensis, Bacillus coagulans, Bacillus subtilis, Bacillus amyloliquefaciens, Bacillus licheniformis*, and any combinations thereof. In another aspect, the composition is added to a growth, sporulation, or a fermentation medium to promote or enhance spore germination, growth, viability, yield, metabolite production, or any combinations thereof of the one or more microorganisms, wherein the growth medium comprises nutrient broth (NB), nutrient agar (NA), Luria-Bertani broth (LB), Mueller-Hinton cation-adjusted broth (MH), a sporulation broth, eosin-methylene blue agar (EMB), yeast and mold (YM), blood agar, MacConkey agar, Hektoen enteric agar (HE), mannitol salt agar (MSA), Terrific Broth (TB), xylose lysine deoxycholate (XLD), RPMI-1640 media, minimally-based media, molasses-based media, buffered charcoal yeast extract agar, or any combinations or modifications thereof. In another aspect, the composition is added to the growth medium at a concentration ranging from 0.01%-15%, 0.5%-10%, or 1%-5%. In another aspect, the extract is made by a method comprising the steps of: blending the fruit with distilled water in a processor to form a smooth mixture; centrifuging the mixture to separate a supernatant and a sediment, wherein the sediment is discarded and the supernatant is taken for further processing; sterilizing the supernatant; performing a second centrifugation if necessary on the sterilized supernatant to remove any separated sediment or debris; and purifying the sterilized supernatant by a membrane filtration process, wherein the membrane filtration results in an isolation of a fraction of the supernatant of a desired molecular weight range comprising one or more active components responsible for the promotion or enhancement of the germination, the growth, the viability, the yield, the metabolite production, or any combinations thereof of the one or more microorganisms. In one aspect, the method further comprises the optional step of processing the extract with the one or more active components by one or more techniques selected from lyophilization, vacuum centrifugation, spray drying, or any combinations thereof. In another aspect, the fraction comprising the active components comprises one or more active components in the molecular weight range of 250-1,000 Daltons. In another aspect, the membrane filtration process is performed using a flat-sheet or a hollow fiber membrane, tubular membrane, spiral wound, hollow fiber, pressurized, immersed, or ceramic filtration. In another aspect, the fruit is ripened and then frozen prior to processing.

Yet another embodiment of the present invention includes a method for promoting or enhancing germination, growth, viability, yield, metabolite production, or any combinations thereof of one or more bacterial strains, yeast strains, or both comprising the steps of: providing a fermentation or growth medium for a cultivation or growth of the one or more bacteria, yeast, or both comprising an extract obtained from one or more bananas or plantains to the fermentation or the growth medium; adding an inoculum or spores of the one or more unknown bacterial strains, yeast strains, or both; and monitoring the growth, viability, yield, metabolite production, or any combinations thereof of one or more bacterial strains, yeast strains, or both. In one aspect, the bacterial strains, the yeast strains, or both in the inoculum comprise unknown strains or previously characterized strains. In another aspect, the method further comprises the optional steps of: isolating the one or more bacterial strains, yeast strains, or both from the fermentation or growth medium; separating or isolating the metabolites from the bacterial strains, yeast strains or both; performing a genetic characterization to identify one or more unknown strains from the isolated bacterial strains, yeast strains, or both. In one aspect, the bacterial strain is a *Bacillus* species. In another aspect, the yeast strain is a *Saccharomyces* species. In another aspect, the metabolites comprise proteins, antibiotics, lipids, surfactants, sugars, alcohols, or any combinations thereof. In another aspect, the extract is made by a method comprising the steps of: providing one or more bananas or plantains; preparing the bananas or plantains for processing by a method comprising the steps of: inspecting the bananas or plantains for any portions showing discoloration, bruises, microbial growth, environmental stress, or any combinations thereof; cutting and discarding any portion of the bananas or plantains showing discoloration, bruises, microbial growth, environmental stress, or any combinations thereof; cutting and discarding the ends of the bananas or plantains; placing the bananas or plantains in a blender or a processor along with distilled water; blending the bananas or plantains with the distilled water in a processor to form a smooth mixture; centrifuging the mixture to separate a supernatant and a sediment, wherein the sediment is discarded and the supernatant is taken for further processing; sterilizing the supernatant; performing a second centrifugation if necessary on the sterilized supernatant to remove any separated sediment or debris; and purifying the sterilized supernatant by a flat sheet or hollow fiber membrane filtration process, wherein the membrane filtration results in an isolation of a fraction of the supernatant of a desired molecular weight range comprising one or more active components responsible for the promotion or enhancement of the germination, the growth, the viability, the yield, the metabolite production, or any combinations thereof of the one or more microorganisms. In another aspect, the inoculum of microorganisms is sub-optimal. In another aspect, the microorganisms comprise viable, but not culturable (VBNC) microorganisms. In another aspect, the inoculum comprises the one or more microorganisms in a lag phase or an exponential phase of a microbial growth cycle. In another aspect, the fruit is ripened and then frozen prior to processing.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
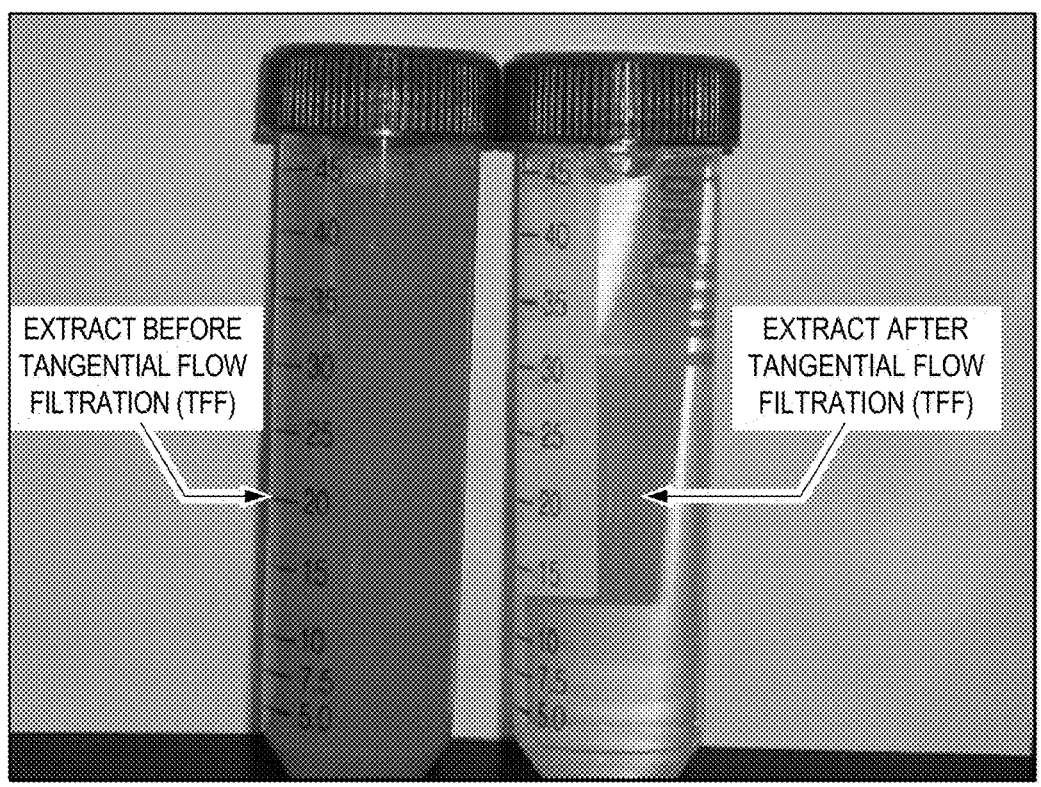
FIG. 1 is a photograph showing the visual difference between starting raw material (left tube) and appearance following TFF using a 1,000 Molecular Weight Cut-Off (MWCO) filter (right tube)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term banana refers to the fruit obtained from any member belonging to the genus *Musa*. The term "unripe banana" refers to a banana skin appearance greater than 80% green, hard to touch. The term "ripe banana" refers to a banana having a skin uniformly yellow, little brown spotting, firm to touch. The term "overripe banana" refers to a banana skin uniformly brown, very soft to the touch The term "tangential flow filtration (TFF)" as used herein refers to a method in which a feed stream is passed tangentially over a membrane in which particles larger than the pore size of the membrane pass (flow) over the filter and the particles smaller than the pore size flow through the filter and are collected as the permeate. The methodology is also known as cross flow filtration.

As used herein the term "BACLYTE™" or BACLYTE" refers to the extract compositions of the present invention and embodiments thereof.

A wide variety of medias may be used with the present invention, which are well-known to those of skill in the art and as taught in many molecular biology reference manuals such as Maniatis, Molecular Cloning: a Laboratory Manual, or Current Protocols In Molecular Biology, relevant portions and recipes incorporated herein by reference. One example of a media is a "minimal" media, which is a media that is generally free of complex ingredients such as animal proteins that are undefined. Minimal media generally include salts, an energy (carbon) source, and any necessary buffers that are adjusted to permit growth of the target microorganism and into which the present invention is added.

The present invention describes an extract from banana or any member from the genera *Musa* (family Musaceae) and a method of preparing the same to be used in enhancing or promoting the growth of bacteria, yeasts, or other microorganisms by itself or as part of a growth medium. Tangential flow filtration (TFF) is the method for processing the raw material of the present invention to enhance or promote growth of bacteria, yeasts, and other microorganisms.

One of the biggest advantages in the using the extract prepared as described hereinabove (and referred to as BACLYTE™) is that one can utilize minimal media which makes the task of purifying the commercially valuable product from the media much easier and more profitable since the steps needed to get rid of the media ingredients can be eliminated. Further, the composition of the present invention promotes growth in media that does not contain animal products thereby allowing bacteria/yeasts to grow that can then be incorporated, as well as the products that are made, into are vegetarian products which is a huge market. Currently, manufacturers of vegetarian products need to solve issues associated with growing microbes in media that contains animal products and the BACLYTE™ composition of the present invention addresses this problem.

The method of preparation of a raw material has been described in U.S. Patent Application Publication Number 2009/0087517 A1 (relevant portions incorporated herein by reference). Ripe Cavendish bananas were peeled and the skins were discarded. The banana fruit was then inspected for any discoloration or bruises and if found were cut off and not used. The ends of the fruit (approximately one-quarter inch in length) were also cut off and discarded. The fruit was then weighed and placed into a standard high-quality food processor (VitaMix, Cleveland, Ohio). An equal volume of distilled water was added to the food processor and the mixture was blended on highest speed achievable on the blender for 90 seconds. Following blending, the blended juice was poured into centrifuge containers and spun at 3900 rpm corresponding to "g force" value of 3230 (speed of 3900 rpm and radius of 18 cm). Following 30 minute centrifugation, the supernatant was collected into a large 1L glass bottle and the solid debris at the bottom of the container was discarded. The supernatant was then autoclaved at standard autoclave temperature (121° C., 25 minutes, 20 lbs. pressure) to achieve sterility. As a consequence of autoclaving, some precipitation in the supernatant occurs. To remove this precipitated material, the autoclaved supernatant was allowed to cool and then subjected to a round of centrifugation according to the same parameters for the initial processing of the blended fruit. It will be understood by the skilled artisan that centrifugation to remove the precipitation in the supernatant may not always be necessary. Following centrifugation the supernatant was collected and any pelleted solid debris as a consequence of centrifugation was discarded.

TFF procedure for preparation of the compositions of the present invention (BACLYTE™) from raw material: Raw material processed as described hereinabove was loaded into 2 different TFF systems. The first was a flat sheet TFF system manufactured by Pall Corporation (Exton, Pa.) and the second a hollow fiber TFF system manufactured by Spectrum Laboratories (Rancho Dominguez, Calif.). The MWCO of the filter systems ranged from 1000 to 3000 MW. Sample was directly applied to the TFF systems according manufacturer's specifications and run at the recommended pressure for the particular TFF membrane. The permeate-containing material was collected during the separation run. FIG. 1 shows the visual difference between starting raw material (left tube) and appearance following TFF using a 1000 MWCO filter (right tube). In order to further characterize the chemical differences between these preparations chemical analyses was performed using a battery of analytical tests performed by SDK Laboratories (Hutchinson, Kans.) as shown in Table 1.

TABLE 1

Results of Chemical analysis on samples before and after TFF prep.

| Analysis | Tube #1 (Before TFF prep) | Tube #2 (After TFF prep) |
| --- | --- | --- |
| Dry matter | 4.90% | 2.90% |
| Protein, crude | 0.35% | 0.11% |
| Ash | 1.04% | Less than 0.1% |
| Calories | 15 | 12 |
| Carbohydrates | 4 | 3 |
| Potassium | 0.17% | 0.10% |
| Magnesium | 0.02% | 0.01% |
| Cooper | 0.41 ppm | Less than 0.2 ppm |
| Iron | 0.91 ppm | 0.42 ppm |
| Manganese | 0.52 ppm | 0.32 ppm |
| Brix | 10.40 s.u. | 6.50 s.u. |
| Vitamin C | 15.8 mg/100 ml | 2.7 mg/100 ml |

Figure 2:
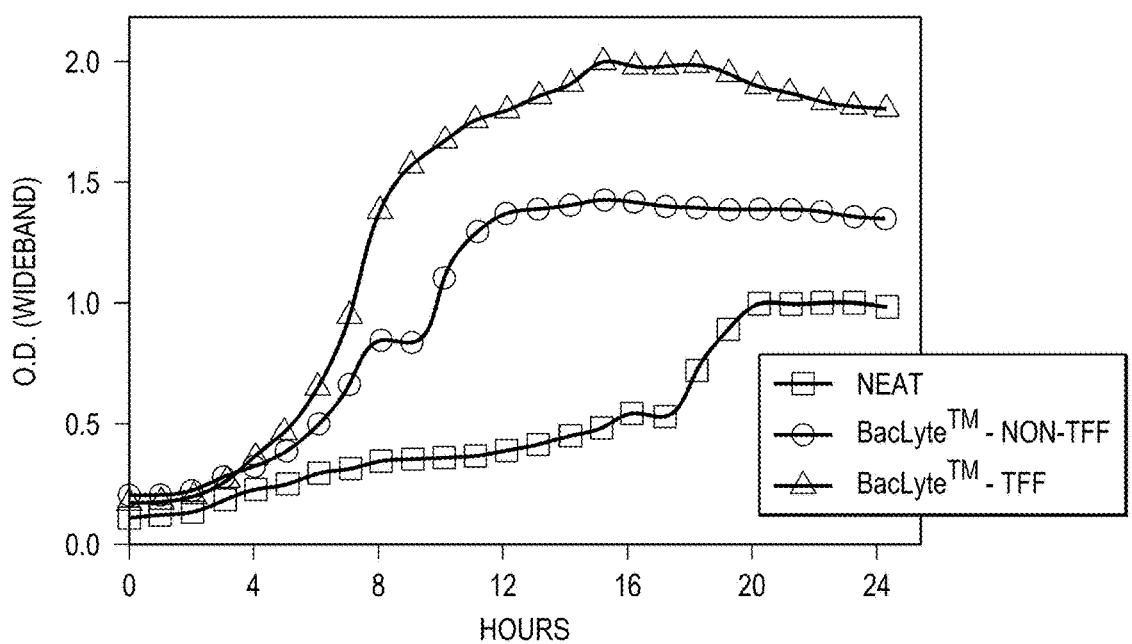
FIG. 2 shows the bacterial promoting activity in a *Bacillus subtilis*-based bacterial growth assay.

The preparations shown in FIG. 1 were then tested for bacterial promoting activity in a *Bacillus subtilis*-based bacterial growth assay (FIG. 2). As shown in FIG. 2, the 1000 Daltons permeate was significantly better at induced the germination and subsequent growth of *Bacillus subtilis*.

The work presented hereinabove was performed with green, ripe and overripe bananas showing that all ripeness stages contain significant amounts of bacterial and yeast enhancing activity. Further, it appears that the overripe bananas provides the easiest method of preparation due to less solids interfering with the TFF procedure and at the same time producing the highest specific activity per volume as compared to other ripeness stages.

Work with other non-Cavendish members of *Musa*, such as plantains, showed similar ability to prepare as above and obtain fractions of high activity following TFF.

Size separation to further clarify most potent molecular range of activity: In order to further define the molecular range in which the most active fractions to enhance bacterial activity reside, the 1000 Da MWCO permeate was loaded into dialysis capsules with a 500 Da MWCO. It will be understood that though the present inventors chose fractions in the molecular weight range of 500-1000 Daltons for the studies of the present invention, other fractions having a higher or lower molecular ranges may also be used for promoting or enhancing germination, growth, viability, yield, metabolite production, or any combinations thereof of one or more microorganisms Following overnight dialysis the retentate was tested in a *Bacillus subtilis*-based bacterial growth assay. The results shown in FIG. 2 demonstrate that the majority of activity resides in a molecular size window of approximately 500-1000 Da MWCO.

Once the TFF permeate is obtained, it may be further concentrated by use of vacuum centrifugation and/or lyophilization followed by reconstitution in a minimal volume of water. This will yield a more highly concentrated specific bacterial/yeast enhancing activity per volume than the original volume of permeate. Other methods which can be employed include, and are not limited to, spray drying.

The extract prepared as described hereinabove promotes or enhances bacterial spore germination, bacterial growth, and growth of other microorganisms including yeast and other fungal species as illustrated in the examples presented herein below. It must be pointed out that in all of these examples presented herein a low inoculum of microbe is used. Currently high doses of microbes are generally used to get the process going. The advantage of using low amounts of microbes is that there will be a significant savings to companies which producing inoculum as the BACLYTE™ can be bundled with the product, thereby increasing product revenue margins and realizing better cost savings. It will be understood to the person skilled in the art that the results presented herein below for the low amounts of microbes is expected to apply for the higher doses of inoculum.

EXAMPLE I

The compositions of the present invention (BACLYTE™) was employed to increase germination of *Bacillus* species spores. The *Bacillus* species spores can be obtained from state university collections such as the *Bacillus* Genetic Stock Center at the Ohio State University (Columbus, Ohio) in the form of spore-impregnated filter disks.

Figure 3:
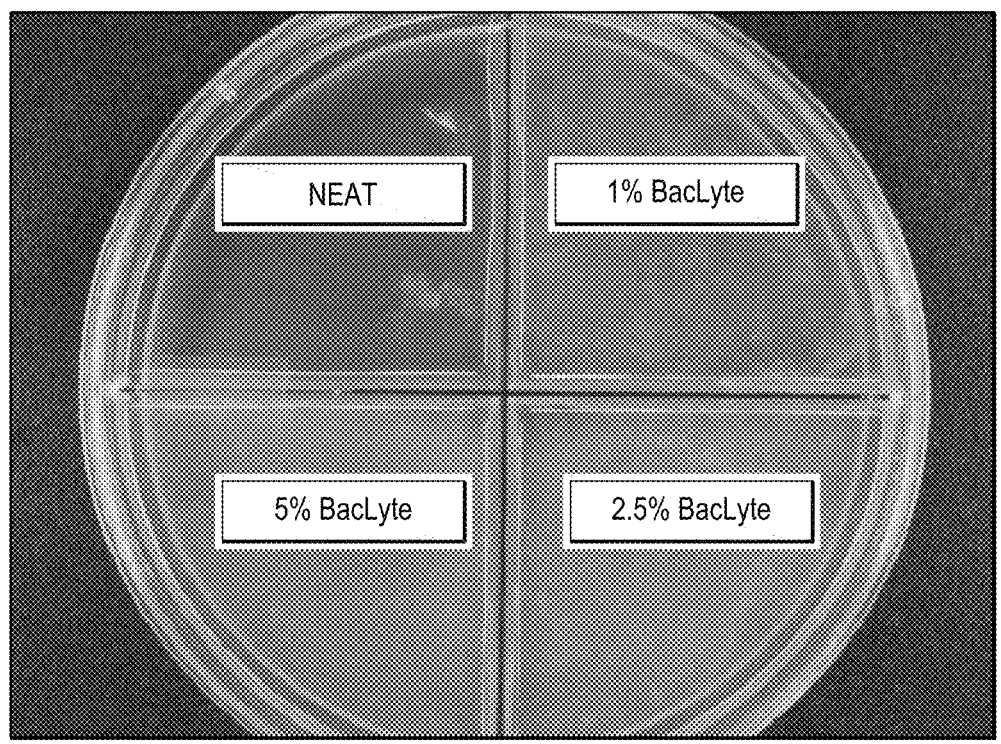
FIG. 3 demonstrates the ability of increasing concentrations of BACLYTE™ to increase the germination of *B. thuringiensis* spores obtained from a state university maintained culture collection in a liquid-based medium as compared to no BACLYTE™ supplementation ("NEAT") in accordance with embodiments of the disclosure.

An individual spore impregnated filter disk containing the *Bacillus* species spores, *Bacillus thuringiensis* (*Bacillus* Genetic Stock Center (BGSC), Ohio State University, Columbus, Ohio, catalog 4A3) was placed into two milliliters of room temperature sterile distilled water. The disk was then agitated by high speed vortexing for a few seconds every minute for five minutes to dislodge the spores from the disk into the solution. Ten microliter aliquots of the spore-containing solution was then removed from the tube and introduced into separate tubes each containing ten milliliters of Luria-Bertani broth (LB broth) that had been supplemented with either diluent ("NEAT"), one percent final concentration of the compositions of the present invention (BACLYTE™), two and a half final concentration of the compositions of the present invention (BACLYTE™) or five percent final concentration of the compositions of the present invention (BACLYTE™). The tubes were then thoroughly mixed using a vortex mixer and six milliliters from each tube was pipetted into individual quadrants of an X-quadrant Petri dish. The Petri dish was then incubated in a 37° C. incubator that was humidified at 85% relative humidity using distilled water as a humidity source. Growth of the individual quadrants was monitored using a camera-based documentation system that captured images of growth at defined intervals according to a software-based program (UVP ColonyDoc-It™ Imaging Station). A representative image capture at 22.75 hours following the start of incubation is shown in FIG. 3. As seen in FIG. 3, increasing concentrations of the compositions of the present invention (BACLYTE™) resulted in greatly increased amount of spore germination into vegetative (growing) *B. thuringiensis* growth as evidenced by the increased opacity of the liquid in the quadrants as compared to the non-BACLYTE™ (or "NEAT") culture

EXAMPLE II

The compositions of the present invention (BACLYTE™) was employed to increase germination of *Bacillus* species spores. The *Bacillus* species spores can be obtained from commercial supply companies such as Microbiologics (St. Cloud, Minn.) in the form of lyophilized pellets such as those in a LYFO DISK® product.

A single lyophilized pellet of *Bacillus coagulans* from LYFO DISK® product #7050 was removed from the manufacturer's vial and placed into a small sterile plastic tube. As according to manufacturer's instructions, 0.5 ml of sterile saline was added to the spore pellet containing tube and the pellet was crushed using a sterile swab. Next, 0.1 ml of spore suspension was removed and added to 3.9 ml of Nutrient Broth (NB) containing either diluent ("NEAT") or the compositions of the present invention (BACLYTE™) at 1%, 2.5% or 5% final concentration. Following complete mixing of all tubes, 0.2 ml aliquots were removed and placed into flat-bottomed wells of a sterile 96 well plate. The plate was then placed into a 37° C. incubator and removed at 48 hours to measure changes in optical density (O.D.) of culture wells using a microplate reader set at 600 nm wavelength (BioTek, Winooski, Vt.). As shown in Table 2, supplementation of NB with the compositions of the present invention (BACLYTE™) resulted in the increased germination of *B. coagulans* spores as reflected in the increased O.D. of cultures supplemented with the compositions of the present invention (BACLYTE™) as compared to those not supplemented ("NEAT").

TABLE 2

Ability of increasing concentrations of the compositions of the present invention (BACLYTE ™) to increase the germination of *B. coagulans* spores obtained from a commercial culture collection source as compared to no BACLYTE ™ supplementation ("NEAT").

| Tube Supplementation | O.D. (580 nm) |
| --- | --- |
| NEAT | 0.104 |
| 1.0% BACLYTE ™ | 0.334 |
| 2.5% BACLYTE ™ | 0.452 |
| 5.0% BACLYTE ™ | 0.357 |

EXAMPLE III

The compositions of the present invention (BACLYTE™) can be employed to increase germination of *Bacillus* species spores. *Bacillus* species spore can be obtained from federal culture collections such as the USDA ARS Collection, also known as the Northern Regional Research Laboratory Collection, in the form of sealed spore-containing ampoules.

Figure 4:
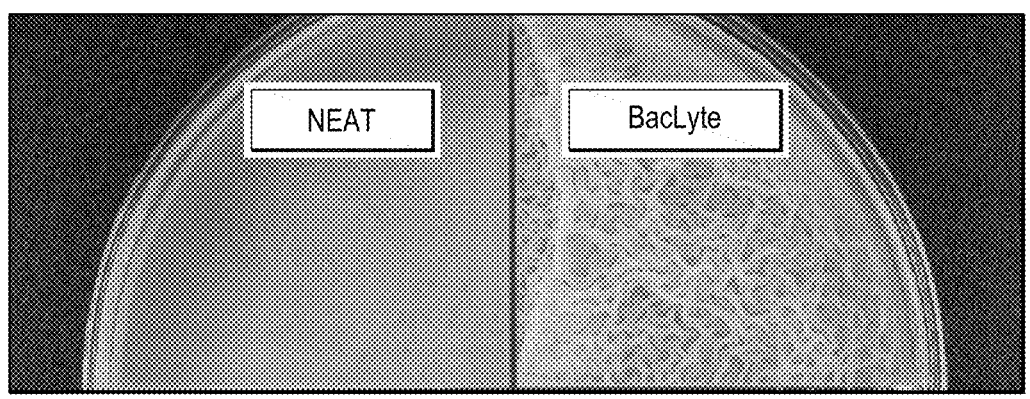
FIG. 4 demonstrates the ability of BACLYTE™ to increase the germination of *B. subtilis* spores obtained from a federal culture collection source in a liquid-based medium as compared to no BACLYTE™ supplementation ("NEAT") in accordance with embodiments of the disclosure.

An individual glass ampoule containing impregnated filter disk containing the *Bacillus* species spores, *Bacillus subtilis* (NRRL catalog B21974) was scored with a glass cutter to remove the top of the ampoule. The spore contents of the ampoule were then placed into a small sterile plastic tube and 1 ml of saline was added to rehydrate the pellet. Following vigorous mixing, 0.1 aliquots were removed from the tube and added to 9.9 ml of LB broth containing diluent ("NEAT") or the compositions of the present invention (BACLYTE™) at a final concentration of 1.5%. Both tubes were then thoroughly mixed using a vortex mixer and 8 ml from each tube was individually placed into a separate quadrant in an X-quadrant Petri dish. The Petri dish was then incubated in a 37° C. incubator that was humidified at 85% relative humidity using distilled water as a humidity source. Growth of the individual quadrants was monitored using a camera-based documentation system that captured images of growth at defined intervals according to a software-based program (UVP ColonyDoc-It™ Imaging Station). A representative image capture at 12.75 hours following the start of incubation is shown in FIG. 4. As seen in FIG. 4, the presence of the compositions of the present invention (BACLYTE™) greatly increased the germination of spores into vegetative (growing) *Bacillus subtilis* growth as evidenced by the dense, luxuriant growth as compared to the non-BACLYTE™ (or "NEAT") culture.

EXAMPLE IV

The compositions of the present invention (BACLYTE™) can be employed to increase germination of *Bacillus* species spores. *Bacillus* species spores can be obtained from federal culture collections such as the USDA ARS Collection, also known as the Northern Regional Research Laboratory Collection, in the form of sealed spore-containing ampoules.

Figure 5:
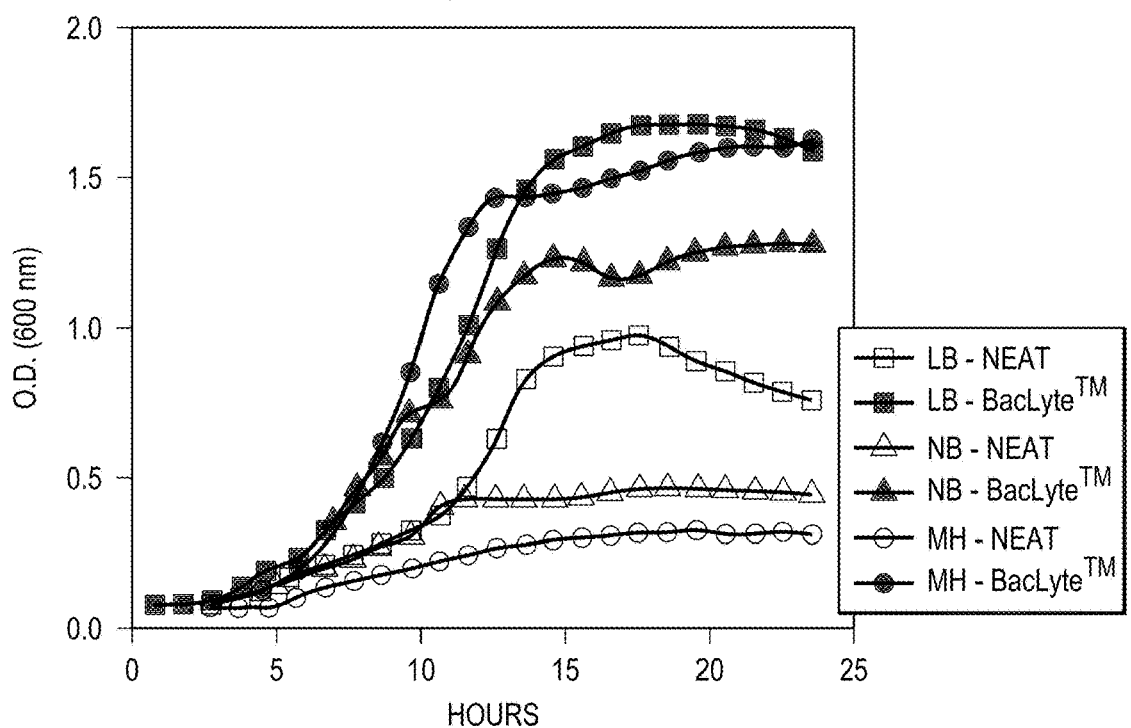
FIG. 5 demonstrates the ability of BACLYTE™ in three different microbiological media to increase the germination of *B. subtilis* spores obtained from a federal culture collection in a liquid-based medium as compared to no BACLYTE™ supplementation ("NEAT") of the three different microbiological media in accordance with embodiments of the disclosure.
Figure 6:
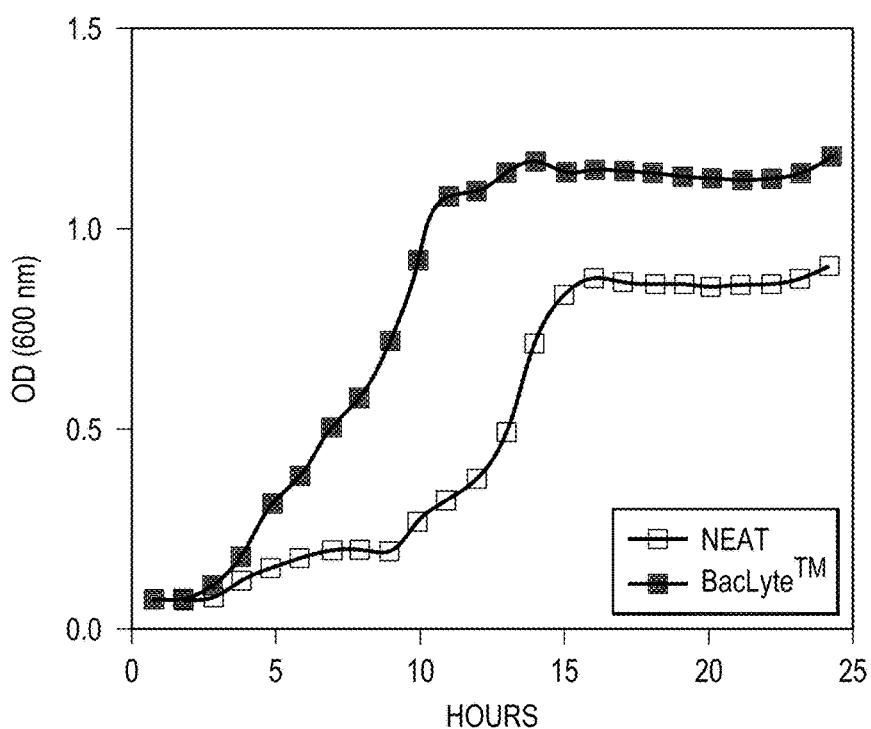
FIG. 6 demonstrates the ability of BACLYTE™ to increase the germination of *B. subtilis* spores obtained from conventional laboratory preparation in a liquid-based medium as compared to no BACLYTE™ supplementation ("NEAT") in accordance with embodiments of the disclosure.
Figure 7:
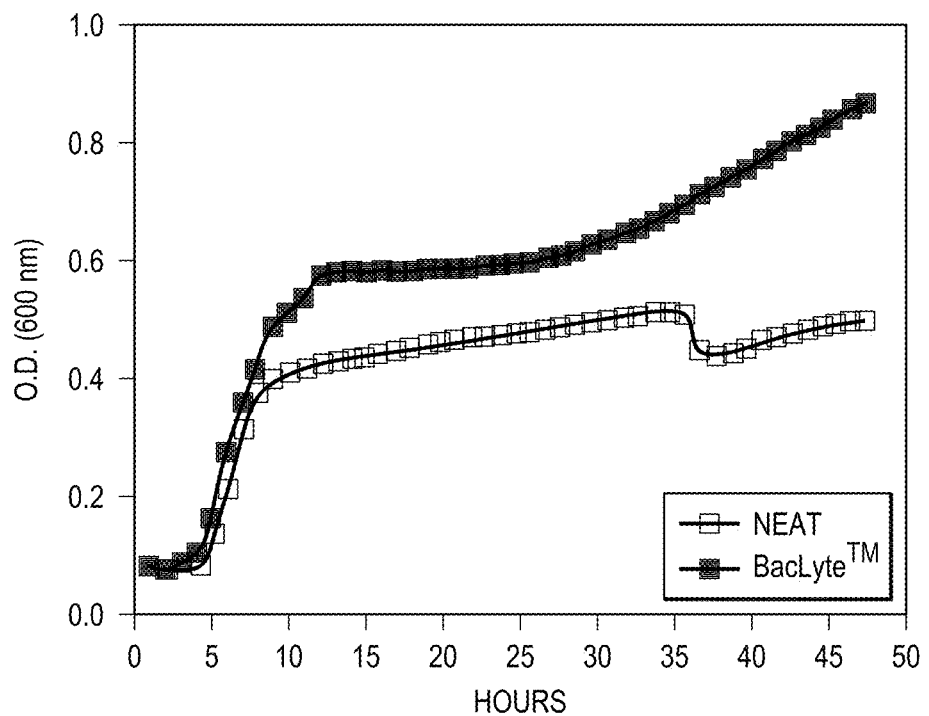
FIG. 7 demonstrates the ability of BACLYTE™ to increase the germination of *B. thuringiensis* spores obtained from conventional laboratory preparation in a liquid-based medium as compared to no BACLYTE™ supplementation ("NEAT") in accordance with embodiments of the disclosure.
Figure 8:
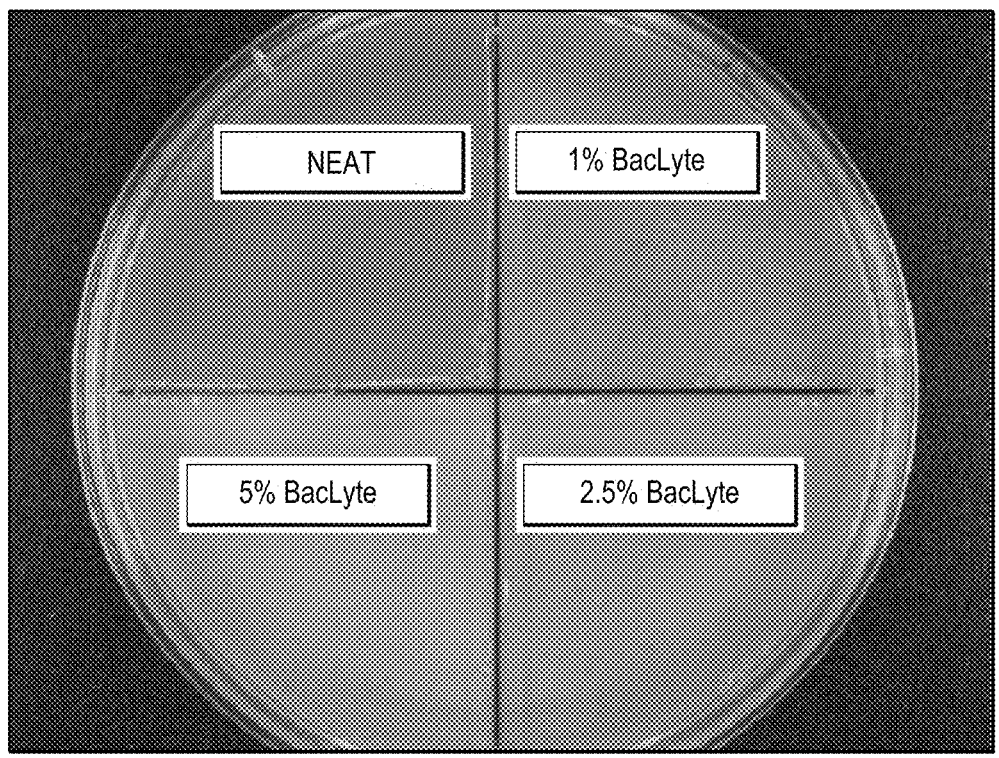
FIG. 8 demonstrates the ability of increasing concentrations of BACLYTE™ to increase the germination of *B. subtilis* spores obtained from a state university maintained culture collection in an agar-based medium collection as compared to no BACLYTE™ supplementation ("NEAT") in accordance with embodiments of the disclosure.

An individual glass ampoule containing impregnated filter disk containing the *Bacillus* species spores, *Bacillus subtilis* (NRRL catalog B21974) was scored with a glass cutter to remove the top of the ampoule. The spore content of the ampoule was then placed into a small sterile plastic tube and 1 ml of saline was added to rehydrate the pellet. Following vigorous mixing, 0.1 aliquots were removed from the tube and added to 9.9 ml of either LB broth, NB or Mueller-Hinton cation-adjusted broth (MH). Into a 100 flat-bottomed well honeycomb plate, 2.5 microliters of either diluent ("NEAT") or the compositions of the present invention (BACLYTE™) was added. Next, 195 microliters of *B. subtilis* NRRL #B21974 containing LB, NB or MH was added to wells and the plate placed in a microbiological analyzer capable of continuous measurement of O.D. of individual wells at specified time points with temperature and shaking control (Bioscreen, Growth Curves USA, Haverhill, Mass.). The plate was incubated in the Bioscreen microbiological analyzer at 37° C. with shaking prior to O.D. measurement for 24 hours. As shown in FIG. 5, supplementation of LB, NB or MH with the compositions of the present invention (BACLYTE™) resulted in the increased germination of spores as reflected in the increased O.D. of cultures supplemented with the compositions of the present invention (BACLYTE™) as compared to those not supplemented ("NEAT").

EXAMPLE V

The compositions of the present invention (BACLYTE™) can be employed to increase germination of *Bacillus* species spores that can be obtained from vegetative cultures which have been grown in a conventional sporulation broth that is commonly used to prepare spores.

One milliliter of a day old LB broth culture of vegetative bacteria from cultures of *Bacillus thuringiensis* (BGSC catalog 4A3) and NRRL *B. subtilis* (NRRL catalog B21974) was inoculated into 50 ml of sporulation broth (HiMedia, Mumbai, India) in a 100 ml bottle. The bottle was then placed in a 37° C. shaker waterbath and rotated at approximately 100 rpm for 5 days. Following 5 day incubation, the contents were removed from the bottle and centrifuged at 4000 rpm for 20 minutes at 18° C. to pellet the bacteria. The bacterial pellet was then re-suspended in 20 ml of saline and then heated to 70° C. for 30 minutes to destroy any vegetative cells leaving only spores intact. From this spore suspension, 20 microliters were removed and added to 20 ml of LB and thoroughly mixed. Into a 100 flat-bottomed well honeycomb plate 300 microliters of *B. thuringiensis* (BGSC catalog 4A3) spore containing LB was added to appropriate well. Next, either diluent ("NEAT") or the compositions of the present invention (BACLYTE™) to give a final concentration of 5% was added to appropriate wells containing spores in LB. The plate was then placed in a microbiological analyzer capable of continuous measurement of O.D. of individual wells at specified time points with temperature and shaking control (Bioscreen, Growth Curves USA, Haverhill, Mass.). The plate was incubated in the Bioscreen microbiological analyzer at 37° C. with shaking prior to O.D. measurement and monitored for 24 hours for *B. subtilis* and 48 hours for *B. thuringiensis*. As shown in FIG. 6, supplementation of *B. subtilis* spores with the compositions of the present invention (BACLYTE™) resulted in the increased germination of spores as reflected in the increased O.D. of cultures supplemented with the compositions of the present invention (BACLYTE™) as compared to those not supplemented ("NEAT"). Additionally, as shown in FIG. 7, supplementation of *B. thuringiensis* spores with the compositions of the present invention (BACLYTE™) also resulted in the increased germination of spores as reflected in the increased O.D. of cultures supplemented with the compositions of the present invention (BACLYTE™) as compared to those not supplemented ("NEAT").

EXAMPLE VI

The compositions of the present invention (BACLYTE™) can be employed to increase germination of *Bacillus* species spores. *Bacillus* species spores can be obtained from state university collections such as the *Bacillus* Genetic Stock Center at the Ohio State University (Columbus, Ohio) in the form of spore-impregnated filter disks.

An individual spore impregnated filter disk containing the *Bacillus* species spores, *Bacillus subtilis* (BGSC catalog 1A698) was placed into 2 ml of room temperature sterile distilled water. The disk was then agitated by high speed vortexing for a few seconds every minute for 5 minutes to dislodge the spores from the disk into the solution. One hundred microliter aliquots of the spore-containing solution was then removed from the tube and introduced into separate tubes each containing 9.9 ml of molten (52° C.) Nutrient agar (NA) that had been supplemented with either diluent ("NEAT"), 1% final concentration of the compositions of the present invention (BACLYTE™), 2.5% final concentration of the compositions of the present invention (BACLYTE™) or 5% final concentration of BACLYTE™. The tubes were then thoroughly mixed using a vortex mixer and the contents of each tube poured into individual quadrants of an X-quadrant Petri dish. After 15 minutes at room temperature during which the molten agar hardened into solid agar, the Petri dish was then incubated in a 37° C. incubator that was humidified at 80% relative humidity using distilled water as a humidity source. Growth of the individual quadrants was monitored using a camera-based documentation system that captured images of growth at defined intervals according to a software-based program (UVP ColonyDoc-It™ Imaging Station). A representative image capture at 15 hours following the start of incubation is shown in FIG. 8. As seen in FIG. 8, increasing concentrations of the compositions of the present invention (BACLYTE™) resulted in greatly increased amount of spore germination into vegetative (growing) *Bacillus subtilis* growth as evidenced by the increased opacity of the agar quadrants as compared to the non-BACLYTE™ (or "NEAT") culture.

EXAMPLE VII

The compositions of the present invention (BACLYTE™) can be employed to increase germination of *Bacillus* species spores for direct use in fermentation cultures that can be obtained from laboratory prepared stock spore cultures. One milliliter of a day old LB broth culture of vegetative bacteria from cultures of *Bacillus subtilis* (NRRL catalog B21974) was inoculated into 50 ml of sporulation broth (HiMedia, Mumbai, India) in a 100 ml bottle. The bottle was then placed in a 37° C. shaker waterbath and rotated at approximately 100 rpm for 5 days. Following 5 day incubation, the contents were removed from the bottle and centrifuged at 4000 rpm for 20 minutes at 18° C. to pellet the bacteria. The bacterial pellet was then re-suspended in 20 ml of saline and then heated to 70° C. for 30 minutes to destroy any vegetative cells leaving only spores intact.

From this spore suspension, 50 microliter aliquots of the spore-containing solution was then removed and introduced into separate fermentation bottles each containing 50 ml of LB broth that had been supplemented with either diluent ("NEAT") or the compositions of the present invention (BACLYTE™) to give a final concentration of 2.5%. The bottles were then placed in a 37° C. shaker waterbath and rotated at approximately 100 rpm for 18.5 hours. At the start and end of the incubation period, 0.2 ml aliquots were removed and placed into flat-bottomed wells of a sterile 96 well plate. The plate was then placed into a microplate reader set at 600 nm wavelength (BioTek, Winooski, Vt.) in order to measure changes in optical density (O.D.) of culture wells. As shown in Table 3, supplementation of LB with the compositions of the present invention (BACLYTE™) resulted in the increased germination of spores during the course of fermentation as reflected in the increased O.D. of cultures supplemented with the compositions of the present invention (BACLYTE™) as compared to those not supplemented ("NEAT").

TABLE 3

Ability of the compositions of the present invention (BACLYTE ™) to increase the germination of *B. subtilis* spores employed directly in a fermentation culture system as compared to no BACLYTE ™ supplementation ("NEAT").

| Fermentation Supplementation | O.D. (600 nm) at start | O.D. (600 nm) at 18.5 hrs |
|---|---|---|
| NEAT | 0.045 | 0.889 |
| 2.5% BACLYTE ™ | 0.051 | 1.137 |

EXAMPLE VIII

The compositions of the present invention (BACLYTE™) can be employed to increase germination of *Bacillus* species spores. *Bacillus* species spores can be obtained from state university collections such as the *Bacillus* Genetic Stock Center at the Ohio State University (Columbus, Ohio) in the form of spore-impregnated filter disks.

An individual spore impregnated filter disk containing either the *Bacillus* species spores, *Bacillus amyloliquefa-*

Figure 9:
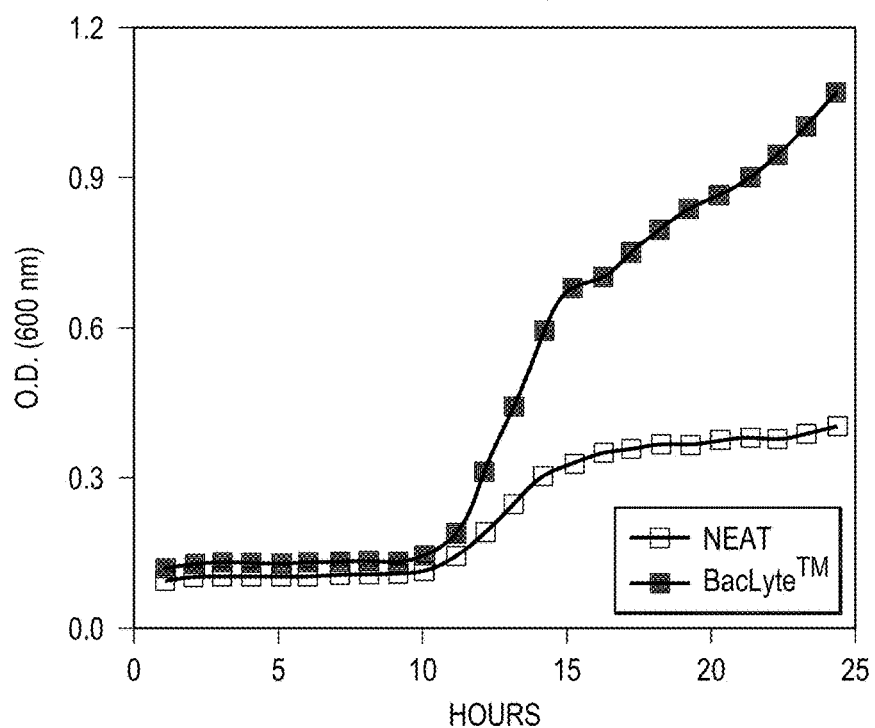
FIG. 9 demonstrates the ability of BACLYTE™ to increase the germination of *B. amyloliquefaciens* spores obtained from a state university maintained culture collection in a liquid-based medium as compared to no BACLYTE™ supplementation ("NEAT") in accordance with embodiments of the disclosure.
Figure 10:
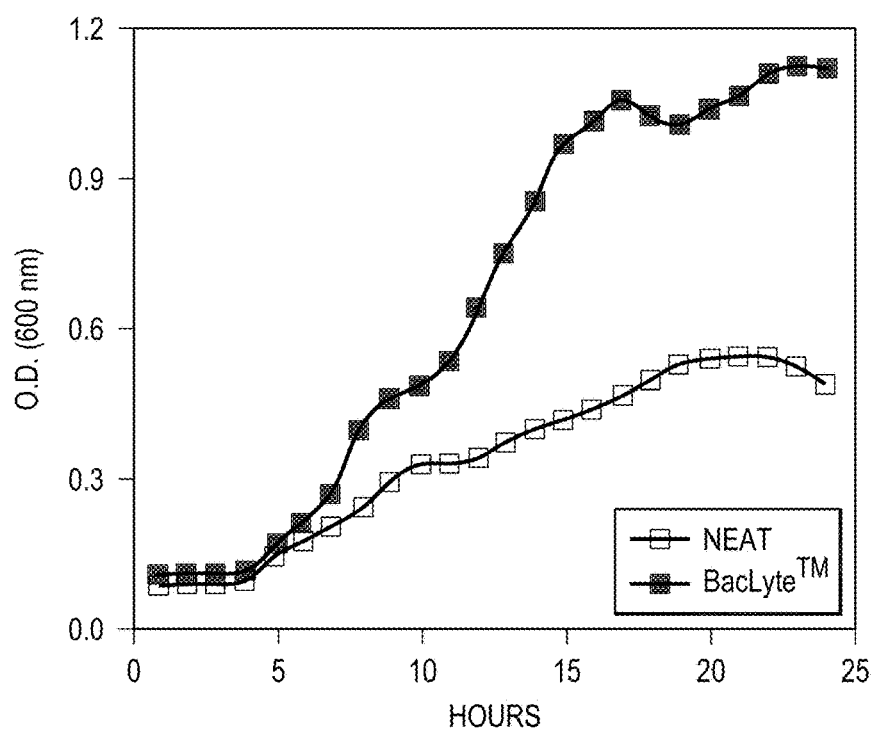
FIG. 10 demonstrates the ability of BACLYTE™ to increase the germination of *B. licheniformis* spores obtained from a state university maintained culture collection in a liquid-based medium as compared to no BACLYTE™ supplementation ("NEAT") in accordance with embodiments of the disclosure.

*ciens* (BGSC catalog 10A18) or *Bacillus licheniformis* (BGSC catalog 5A37) were placed into individual tubes containing 2 ml of room temperature sterile distilled water. The disks were then agitated by high speed vortexing for a few seconds every minute for 5 minutes to dislodge the spores from the disk into the solution. From this spore suspension, 100 microliters were removed and added to 9.9 ml of LB and thoroughly mixed. Into a 100 flat-bottomed well honeycomb plate 300 microliter aliquots of *B. amyloliquefaciens* spore containing LB and *B. licheniformis* spore containing LB were added to appropriate wells containing either diluent ("NEAT") or the compositions of the present invention (BACLYTE™) to give a final concentration of 5%. The plate was then placed in a microbiological analyzer capable of continuous measurement of O.D. of individual wells at specified time points with temperature and shaking control (Bioscreen, Growth Curves USA, Haverhill, Mass.). The plate was incubated in the Bioscreen microbiological analyzer at 37° C. with shaking prior to O.D. measurement at 600 nm wavelength and monitored for 24 hours. As shown in FIG. 9, supplementation of *B. amyloliquefaciens* spores with the compositions of the present invention (BACLYTE™) resulted in the increased germination of spores as reflected in the increased O.D. of cultures supplemented with the compositions of the present invention (BACLYTE™) as compared to those not supplemented ("NEAT"). Additionally, as shown in FIG. 10, supplementation of *B. licheniformis* spores with the compositions of the present invention (BACLYTE™) also resulted in the increased germination of spores as reflected in the increased O.D. of cultures supplemented with the compositions of the present invention (BACLYTE™) as compared to those not supplemented ("NEAT").

EXAMPLE IX

Figure 11:
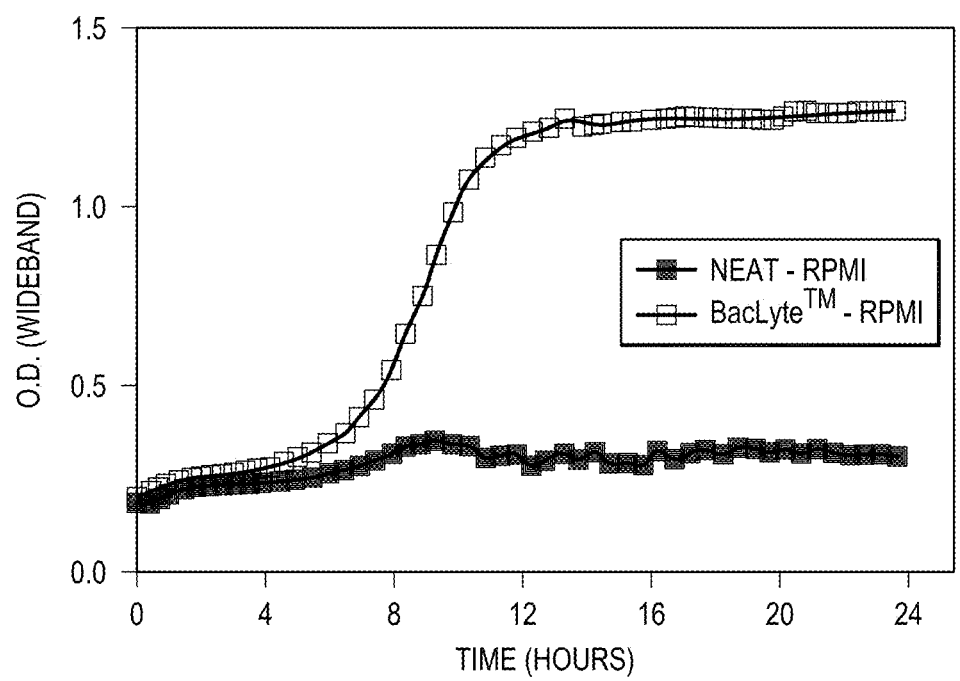
FIG. 11 demonstrates the ability of BACLYTE™ in RPMI-1640 media to increase the growth of *Saccharomyces cerevisiae* K1-V1116 in a liquid-based medium as compared to no BACLYTE™ supplementation ("NEAT") of the media in accordance with embodiments of the disclosure.
Figure 12:
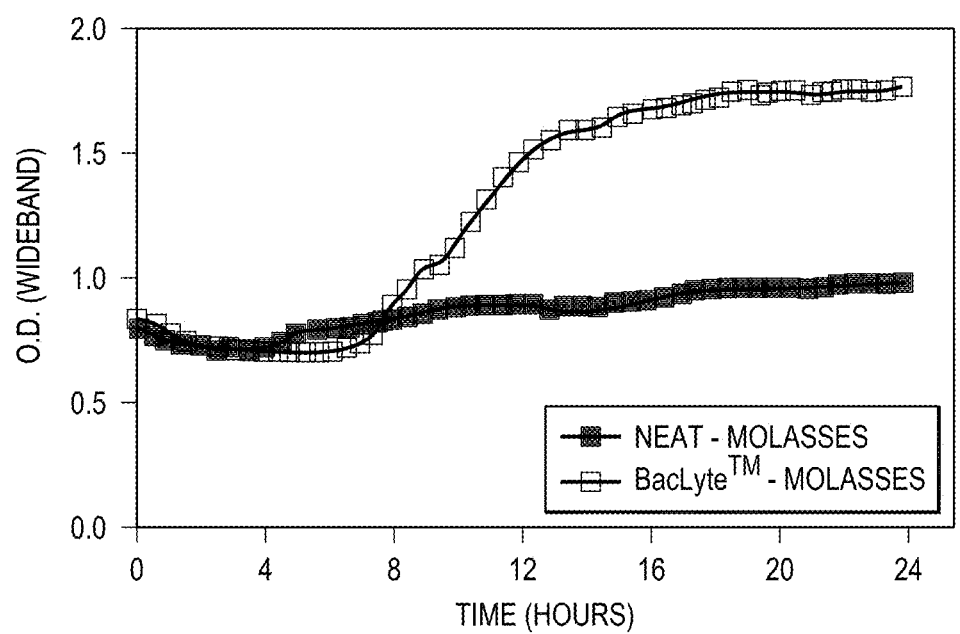
FIG. 12 demonstrates the ability of BACLYTE™ in molasses-based media to increase the growth of *Saccharomyces cerevisiae* K1-V1116 in a liquid-based medium as compared to no BACLYTE™ supplementation ("NEAT") of the microbiological media in accordance with embodiments of the disclosure.

The compositions of the present invention (BACLYTE™) can be employed in yeast growth studies. Approximately 0.35 g of *Saccharomyces cerevisiae* K1-V1116 obtained from Lallemand (Montreal, Canada) was placed into a 50 ml polypropylene tube and 10 ml of double-distilled water (DDW) was added. The contents of the tube were then thoroughly mixed. After standing for 10 minutes with intermittent gentle shaking of tube contents every 2-3 minutes, 20 microliters of the *S. cerevisiae* K1-V1116 suspension was added to 20 ml of RPMI-1640 medium without phenol red and without L-glutamine (Lonza catalog #12-918F, Lonza, Walkersville, Md.) and 20 microliters was added into 20 ml of a 10% molasses medium. The 10% molasses medium was made by mixing 2.5 ml of molasses (Grandma's Original Molasses, Gold Label, B&G Foods, Parsippany, N.Y.) with 22.5 ml of DDW. Next, into a 100 flat-bottomed well honeycomb plate 300 microliters of *S. cerevisiae* K1-V1116 containing RPMI-1640 or 300 microliters of *S. cerevisiae* K1-V1116 containing 10% molasses RPMI-1640 (RPMI-1640 without phenol red and without L-glutamine, Lonza catalog #12-918F, Lonza, Walkersville, Md.) was added to appropriate wells. RPMI-1640 is a defined medium not routinely employed for growth of yeast as it does not support growth well. Ability to grow yeast in such a medium would be advantageous as it would simply extraction and purification of products that yeast may produce in culture. Molasses-based medium is a medium typically employed for the growth of yeast. Next, either diluent ("NEAT") or the compositions of the present invention (BACLYTE™) to give a final concentration of either 1 or 5% was added to appropriate wells containing *S. cerevisiae* K1-V1116 in either RPMI-1640 or 10% molasses. The plate was then placed in a microbiological analyzer capable of continuous measurement of O.D. of individual wells at specified time points with temperature and shaking control (Bioscreen, Growth Curves USA, Haverhill, Mass.). The plate was incubated in the Bioscreen microbiological analyzer at 30° C. with shaking prior to O.D. measurement and monitored for 24 hours. As shown in FIGS. 11 and 12, supplementation of *S. cerevisiae* K1-V1116 with the compositions of the present invention (BACLYTE™) resulted in the increased rate of growth as reflected in the increased O.D. of cultures supplemented with the compositions of the present invention (BACLYTE™) as compared to those not supplemented ("NEAT").

It will be clear from FIGS. 11 and 12 that the promotion of growth with the compositions of the present invention (BACLYTE™) with a small inoculum size, which offers considerable economic and production advantages as previously described. The RPMI-1640 medium that is used in FIG. 11 is not the normal growth medium for yeast, though it would be highly desirable to use RPMI-1640 or a similar medium to grow yeast as there are not proteins in the medium which would interfere with downstream processing of the component of interest that the yeast may make. The compositions of the present invention (BACLYTE™) of the present invention makes it possible to grow yeast or other similar species grow in RPMI or a similar medium where they are not expected to grow under normal circumstances.

The advantage of the compositions of the present invention (BACLYTE™) in growing yeast is further seen in FIG. 12 as it is in a molasses-based medium, which should support good growth of the NEAT culture. However, the strain used herein is a wine strain and it may not be like yeast however in the presence of the compositions of the present invention (BACLYTE™) it shows extremely good growth.

EXAMPLE X

Preparation Involving Frozen Bananas

An additional modification to the processing protocol for the preparation of the compositions of the present invention (BACLYTE™) is the use of bananas that are first frozen overnight and then thawed prior to their use in the compositions of the present invention (BACLYTE™) preparation protocol. The skilled artisan will recognize, based on the teachings of this application, that other sources of frozen banana (or fruit) and frozen banana (or fruit) extracts can be used with the present invention, e.g., flash frozen bananas, banana flakes, banana puree and lyophilized bananas or other fruits. Thawed, previously frozen, bananas yield a much softer texture with evident release of liquid from their structure giving them the characteristic mushy texture thereby lending to easier processing and extraction of a greater amount of the compositions of the present invention (BACLYTE™) active material. For the data shown in FIG. 13, Cavendish bananas were allowed to ripen to an overripe stage as defined in the disclosure at room temperature. Once the fully overripe stage had been achieved, bananas were either left at room temperature or placed in a −20° C. or a −80° C. freezer for 24 hours. In this example, after the 24-hour freezing period ended, the bananas were removed from the freezers and allowed to fully thaw, e.g., at room temperature (however, thawing at other temperatures can also be used, e.g., 4° C. or even heating the frozen banana directly (with or without the peel) by immersing in liquid, an oven, a microwave oven, an infrared oven, that will increase the rate of thawing, e.g., up to 25° C., 37° C., 40° C. or even 45° C. However, it is possible to freeze at other temperatures and/or shorten the time in which the bananas are frozen by, e.g., freezing in liquid nitrogen for a few seconds to minutes. The soft skin was then easily peeled away and the mushy interior was processed to prepare the compositions of the present invention (BACLYTE™) as described hereinabove. The resultant the compositions of the present invention (BACLYTE™) preparation were then tested as shown in FIG. 13 for their ability to increase the germination of *B. subtilis* spores.

Figure 13:
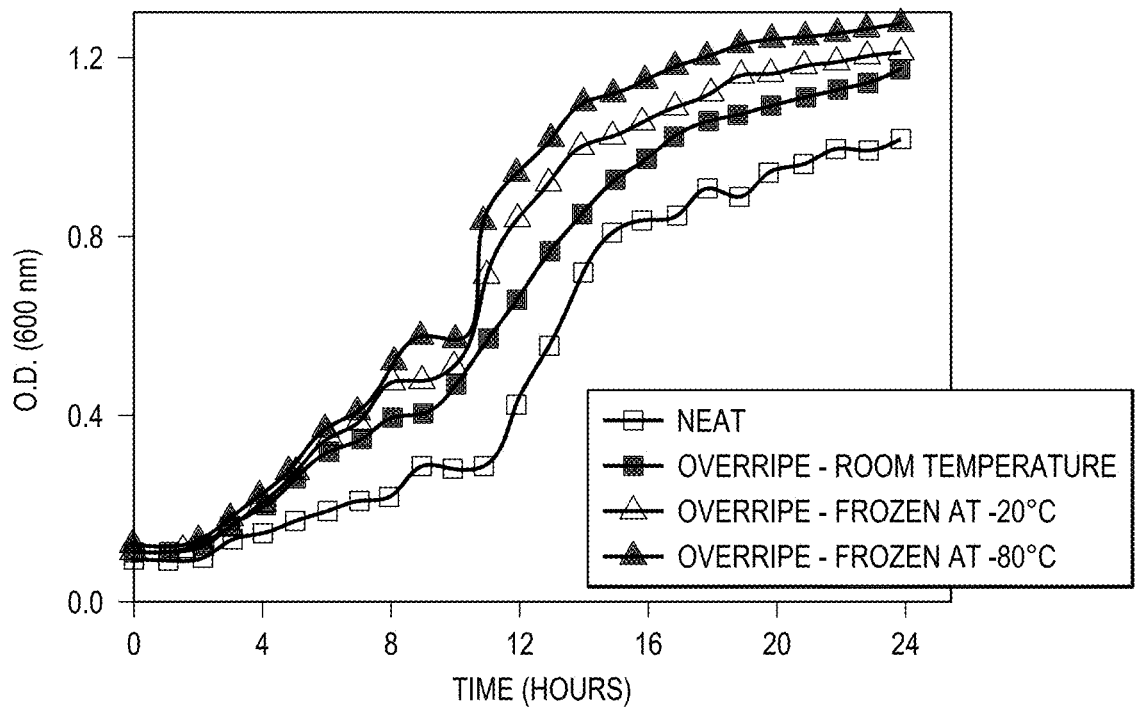
FIG. 13 shows the ability of different preparations of BACLYTE™ prepared from overripe Cavendish bananas that had been frozen at two different temperatures or not and then thawed prior to processing for BACLYTE™.

FIG. 13 demonstrates the ability of different preparations of the compositions of the present invention (BACLYTE™) prepared from overripe Cavendish bananas that had been frozen at two different temperatures, or not, and then thawed prior to processing for the compositions of the present invention (BACLYTE™) to increase the germination of *B. subtilis* B29174 spores obtained from a state university maintained culture collection (BGCS) in a liquid-based medium as compared to no BACLYTE™ supplementation ("NEAT") in accordance with embodiments of the disclosure. As shown in FIG. 13, there was a significant increase in the growth as compared to the NEAT control. Specifically, it was found that as the temperature decreases the yield of active material increases. This example demonstrates that the present invention can use frozen bananas that are then thawed, making the process easier, increasing the yield of the starting material to increase the total yield of the compositions of the present invention (BACLYTE™). The process can easily be replicated in circumstances where high cost equipment is not available or is not functional. FIG. 13 also shows that the freezing and thawing cycle did not affect the total quality (as shown by the ability to influence spore germination) of the compositions of the present invention (BACLYTE™), but surprisingly, increased the effect of the material on spore germination.

It was found by the present inventions that the use of method and composition the present invention permits the user, for the first time, to use a minimal media that simplifies the purification of the commercially valuable products away from the media in which it is grown. Using the compositions and methods of the present invention, the process of eliminating contaminating media from the active ingredient is easier and eliminates many of the steps needed to purify the final product. It is also possible, using the present invention, to use sub-optimal media to grow the microbes in a manner equivalent or greater than existing media, which contain many more components. Thus, an otherwise minimal media becomes a useful media for microbe growth using the present invention. In fact, it was found that, counter-intuitively, the amount of the inoculum was greatly reduced without a loss in final yield or a robust growth curve commonly associated with a sub-optimal inoculum.

Further, it was found that the compositions of the present invention (BACLYTE™) promotes growth in media that does not contain animal products, which means it can get bacteria/yeasts to grow that can then be incorporated, as well as the products that are made, into vegetarian products. By using a media that does not contain any animal products, it is possible to meet a long-felt need in the industry for growing in an efficient manner microbes in a media that does into contain animal products for use in vegetarian products.

The present invention provides the spray-drying of the compositions of the present invention (BACLYTE™) as a powder preparation. This shows the ability of the compositions of the present invention (BACLYTE™) to be spray dried and thus it can be used as a powder as well as liquid in any application. The present invention also provides encapsulation of the compositions of the present invention (BACLYTE™) with probiotic. Encapsulation of probiotics is viewed as a means to protect probiotics from both the outside environment as well as the harsh conditions of the stomach so it can reach the desired area of the gut in a more robust physiological state. However, methods are continually being sought to improve the viability of the probiotics that are encapsulated. By putting the compositions of the present invention (BACLYTE™) into the capsule (or bead) at the time of encapsulation you have now created an optimal environment especially when the capsule (bead) reaches the gut where it dissolves it now has the compositions of the present invention (BACLYTE™) right next to it to get it growing right away.

The present invention provides spray-drying of the compositions of the present invention (BACLYTE™) along with probiotics. Sprays drying of probiotics have been used in the past with varying results. The present invention provides a growth enhancer such as the compositions of the present invention (BACLYTE™) sprayed dried along with the probiotic results in greater recovery.

The present invention provides a composition (i.e., BACLYTE™) that is further processed using spray drying to produce an active powder. The spray drying of sugar-rich fruit juices such as those from bananas, mangoes and pineapples typically produce very sticky powders due to a number of processing variables such as the glass transition temperature (Tg) and the sticky point temperature (Ts). One of the most common methods employed in industry to produce non-sticky fruit juice powder preparations is the addition of higher Tg components, such as maltodextrin, to the juice prior to the spray drying. For the production of the present invention as a powder, 500 ml of liquid the compositions of the present invention (BACLYTE™) was mixed with 125 grams of maltodextrin (Spectrum Chemical Labs, 10.5% dextrose equivalent; final maltodextrin concentration of 25% w/v). Complete dissolution of the maltodextrin in the compositions of the present invention (BACLYTE™) was accomplished with gentle heating to 37° C. for 15-20 minutes with stirring. The compositions of the present invention (BACLYTE™) was then spray dried using a Buchi B-290 mini-spray dryer with inlet temperature of 141° C. and outlet temperature of 73° C. resulting in a whitish, non-sticky powder.

Figure 14:
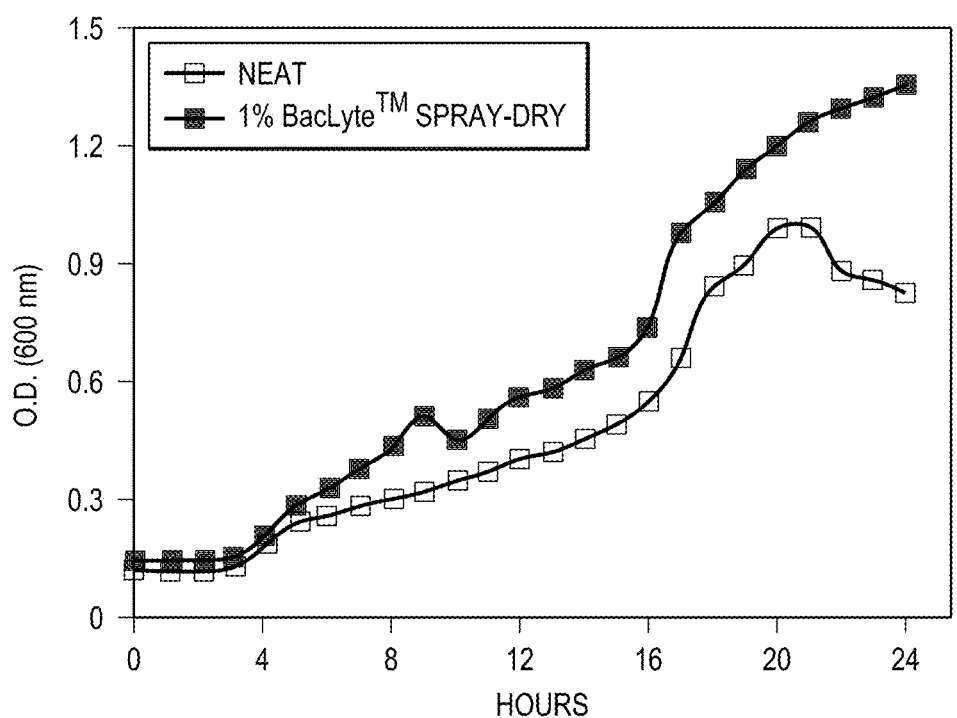
FIG. 14 shows the supplementation of *B. subtilis* spores with spray dried BACLYTE™ showing an increase in germination of spores as reflected in the increased O.D. compared to those not supplemented ("NEAT").

Testing of biological activity of the powder was accomplished by dissolving the powder to yield a 1% solution (w/v) in LB media which was accomplished by end-over-end rotation for approximately 10 minutes after which time the (BACLYTE™) powder of the present invention completely dissolved in the media. The composition of the present invention-containing LB media was then sterilized by filtration through a 0.45 micron syringe filter. NRRL *B. subtilis* (NRRL catalog B21974) spores were then added to either the compositions of the present invention (BACLYTE™)-containing LB media or non-BACLYTE™-containing LB media (NEAT) at a ratio of 1 microliter of spore suspension to 1 ml of media. Into a 100 flat-bottomed well honeycomb plate 300 microliters of each suspension was added and the plate was then placed in a microbiological analyzer capable of continuous measurement of O.D. of individual wells at specified time points with temperature and shaking control (Bioscreen, Growth Curves USA, Haverhill, Mass.). The plate was incubated in the Bioscreen microbiological analyzer at 37° C. with shaking prior to O.D. measurement and monitored for 24 hours for growth. As shown in FIG. 14, supplementation of *B. subtilis* spores with spray dried the compositions of the present invention (BACLYTE™) resulted in the increased germination of spores as reflected in the increased O.D. of cultures supplemented with spray dried the compositions of the present invention (BACLYTE™) as compared to those not supplemented ("NEAT").

For example, the composition of the present invention may include a coating that may be an spray drying. For example long-term storage of probiotics both in the industrial setting and for use in the clinical and alternative medicine settings can be enhanced through the application of spray drying techniques of the present invention. The preparation of spray dried probiotics such as *Lactobacillus* spp. can benefit from the spray drying procedure if spray dried in the presence of the compositions of the present invention (BACLYTE™) since the compositions of the present invention (BACLYTE™) will provide an environment that will allow prolonged storage as a viable product as evidenced by increased rate of recovery following its specific use. *Lactobacillus rhamnosus* was grown overnight in *Lactobacilli* MRS broth to an optical density of approximately 10E9 CFU (colony forming units) per ml. Following 2 times wash in PBS, bacteria were added to either a 10% the compositions of the present invention (BACLYTE™) containing solution (10 ml of the compositions of the present invention (BACLYTE™) in 90 ml of PBS) or to PBS alone (NEAT). Both 10% the compositions of the present invention (BACLYTE™) and NEAT solutions additionally contained 10 w/v of maltodextrin. Solutions were then spray dried using a Buchi B-290 mini-spray dryer with inlet temperature of 151° C. and outlet temperature of 77° C.

Following room temperature storage of bacteria-containing powders for 1 week, 0.1 g of each powder suspension was added to *Lactobacilli* MRS broth and incubated overnight at 37° C. in an anaerobic atmosphere. Following 18 hours incubation, the optical density at 580 nm for each culture was measured. As shown in Table 4, the viability of *L. rhamnosus* was increased with the concomitant addition of the compositions of the present invention (BACLYTE™) at the time of spray drying of the probiotic as compared to NEAT.

TABLE 4

| Spray Dry Supplementation | O.D. (580 nm) |
|---|---|
| NEAT | 0.134 |
| BACLYTE ™ | 0.567 |

In order to assess if the increased optical density was due to true growth of *L. rhamnosus* and not a contaminant acquired during the spray drying procedure, aliquots of both spray dry supplementations were plated on *Lactobacilli* MRS agar. Only colony morphology consistent with *Lactobacillus* sp. was obtained.

The composition of the present invention may be encapsulated. Another technique that has been used extensively by industry to protect probiotics from deleterious environmental conditions as well as provide an efficient means by which to bypass the harsh conditions of the stomach and deliver probiotic bacteria to the desired region of the gut is through the use of encapsulation. By surrounding, or encapsulating, the probiotic in a coating that can be later dissolved away, an effective delivery system can be achieved. The use of the compositions of the present invention (BACLYTE™) as part of the encapsulation procedure, wherein the compositions of the present invention (BACLYTE™) is incorporated into the volume inside the capsule (bead) along with the probiotic, can increase the viability of the probiotic thereby enhancing the overall efficacy of the encapsulation technique. *L. rhamnosus* was grown overnight in *Lactobacilli* MRS broth to an optical density of approximately 10E9 CFU (colony forming units) per ml. Following 2 times wash in PBS, bacteria were added to either a solution containing 5% the compositions of the present invention (BACLYTE™) and 2% sodium alginate or to 2% sodium alginate in PBS alone (NEAT). The encapsulation procedure used is essentially as described by Zhao et al. (World J. Microbiol. Biotechnol., volume 28, pages 61-70, 2012) with the modification that no skim milk was used as part of the process and sodium alginate at a concentration of 2%, not 3%, was used. Following the introduction of the probiotic into the compositions of the present invention (BACLYTE™) or NEAT containing sodium alginate solutions, the suspensions were then extruded through a 20 gauge syringe needle into a 0.3 M CaCl$_2$ solution that was being continually stirred at room temperature. The resultant encapsulation produced large beads in which the probiotic was completely entrapped either in PBS (NEAT) or in PBS supplemented with 5% the compositions of the present invention (BACLYTE™). Beads were collected and washed with 0.1% buffered peptone water and stored at 4° C. Following overnight storage at 4° C., the beads were tested for biological activity by inoculation of 0.5 ml of bead-containing solutions into 9.5 ml of *Lactobacilli* MRS broth and incubation overnight at 37° C. in an anaerobic atmosphere. Following 18 hours incubation, the optical density at 580 nm for each culture was measured. As shown in Table 5, the viability of *L. rhamnosus* was increased with the concomitant addition of the compositions of the present invention (BACLYTE™) at the time of encapsulation of the probiotic as compared to NEAT. It will be understood that the present invention may include encapsulate spores, live bacteria or both.

TABLE 5

| Bead Supplementation | O.D. (580 nm) |
|---|---|
| NEAT | 0.269 |
| BACLYTE ™ | 1.034 |

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

In one embodiment of the invention, the composition may be combined with one or more probiotics. The term "probiotic" means a microorganism that exerts beneficial effects on the health of the host. Any probiotic known in the art may be acceptable in this embodiment provided it achieves the intended result. In a particular embodiment, the probiotic may be selected from *Lactobacillus* species, *Lactobacillus rhamnosus* GG, *Bifidobacterium* species, *Bifidobacterium longum*, *Bifidobacterium animalis* subsp. *lactis* BB-12, the genus *Saccharomyces*, moulds, *Aspergillus*, *Lactobacillus*, *Bifidobacterium*, *Streptococcus*, *Enterococcus*, *Lactobacillus johnsonii*, *Bifidobacterium lactis*, *Streptococcus thermo-*

*philus, Lactobacillus paracasei, Lactobacillus, Streptococcus, Bifidobacterium, Bacteroides, Clostridium, Fusobacterium, Nelissococcus, Propionibacterium, Enterococcus, Lactococcus, Staphylococcus, Peptostreptococcus, Bacillus, Pediococcus, Micrococcus, Leuconostoc, Weissella, Aerococcus, Oenococcus*, pathogenic bacterial species including, but not limited to, *Enterococccus, Clostridium, Escherichia, Klebsiella, Campylobacter, Peptococcus, Heliobacter, Hemophylus, Staphylococcus, Yersinia, Vibrio, Shigella, Salmonella, Streptococcus, Proteus, Pseudomonas, Toxoplasmosis*, and *Rotavirus* species.

In addition the present invention may also include one or more prebiotic compositions in addition to or in place of the probiotic. Prebiotics useful in the present invention may include oligosaccharides, polysaccharides, and other prebiotics that contain fructose, xylose, soya, galactose, glucose and mannose. More specifically, prebiotics useful in the present invention may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosacchairde, chito-oligosaccharide, manno-oligosaccharide, aribino-oligosaccharide, siallyl-oligosaccharide, fuco-oligosaccharide, galacto-oligosaccharide, and gentio-oligosaccharides.

In addition the present invention may also include one more coatings that protect or modify the release of the coated composition. For example, the coating may be an "immediate release" coating used herein to describe a release profile to effect the delivery of an active as soon as possible, that is, as soon as practically made available to a subject, whether in active form, as a precursor and/or as a metabolite. Immediate release may also be defined functionally as the release of over 80 to 90 percent (%) of the composition within about 60, 90, 100 or 120 minutes or less. Immediate release as used herein may also be defined as making the active ingredient available to the subject regardless of uptake, as some drugs may never be absorbed by the host. Immediate release formulations of the active on a carrier, such as rolled or compressed beads, may be formulated such that the surface area is maximized on beads and the active is exposed immediately. Various immediate release dosage forms may be designed readily by one of skill in art to achieve drug delivery to the area depending upon the choice of compression, adhesive materials and/or beading.

For example, the coating may be an "extended release," "controlled release" and "delayed release" coating used to define a release profile to effect delivery of an active over an extended period of time, defined herein as being between about 60 minutes and about 2, 4, 6 or even 24 hours. Extended release may also be defined functionally as the release of over 80 to 90 percent (%) of the active ingredient after about 60 minutes and about 2, 4, 6 or even 8 hours. Extended release as used herein may also be defined as making the active ingredient available to the subject regardless of uptake, as some drugs may never be absorbed by the subject. Various extended and delayed release dosage forms may be designed readily by one of skill in art as disclosed herein to achieve delivery depending upon the choice of coating materials and/or coating thickness.

Another example of a coated particle of the present invention provides a selective, prolonged continuous release of the composition by the application of a diffusion barrier coating to an ion exchange drug-resin complex treated with a solvating agent. Another prolonged release formulation of the present invention includes the addition of a second ionic substance having the same ionic charge as the composition on the resin complex by employing the second ionic substance in the ion form of an exchange resin complex. The manufacture of a formulation of any composition for liquid or solid dosage usage requires that the final formulation have the composition dissolved or suspended in a liquid that possess extended shelf-life stability and exhibit no change in active dosage level over a period of time. Thus, to prepare a liquid formulation of any type drug it may be necessary to employ extenders such as water or syrup and to add flavors, sweeteners, thickening agents, dyes and the like. To control the dissolution profile of the formulation versus the dissolution profile of the same drug in water, the coated particles may also be included in the presence of ionic substances bearing the same ionic charge as the sustained release drug present in the formulation as a coated composition-resin complex. The second ionic material need not be coated with the water-permeable diffusion barrier coating.

The water-permeable, diffusion barrier coating materials can be any of the conventional synthetic or natural film-forming materials with diffusion barrier properties and with no inherent pharmacological or toxic properties. For example, ethylcellulose, a water insoluble film-forming agent, may be used as a diffusion barrier membrane material. A plasticizer, (e.g., Durkex 500 vegetable oil) may be used to improve the film forming characteristics of ethylcellulose and/or to alter the permeability characteristics of the film. The amount of coating used depends on the degree of drug release prolongation desired and is a function of particle size, drug solubility, film permeability and other factors. By varying the amount of coating, and/or by blending coated drug-resin complex with uncoated drug-resin complex, and/or blending different coatings it is possible to selectively modify the preparation's drug dissolution profile as desired.

In general, the major components of the coating should be insoluble in, and permeable to, water. Alternatively, a water-soluble substance, such as methyl cellulose may be incorporated, to alter the permeability of the coating, or an acid-insoluble, base-soluble substance to act as an enteric coating may be used. The water-permeable diffusion barrier will generally include a water insoluble material such as a wax, a fatty alcohol, shellac, zein, shellac, polyvinylpyrrolidone, a water insoluble cellulose derivative, ethyl cellulose, a polymethacrylate, or methyl cellulose. The coating materials may be applied as a solution or suspension in an aqueous fluid or as a solution in organic solvents. In some instances, the present invention may include a water-permeable diffusion barrier in contact with at least a portion of the ionic pharmaceutically active drug in communication with an ionic exchange resin.

In addition the present invention may include other additives conventionally used in pharmaceutical compositions and known to those of skill in the art., e.g., anti-adherents, anti-sticking agents, glidants, flow promoters, lubricants, talc, magnesium stearate, fumed silica), micronized silica, surfactants, waxes, stearic acid, stearic acid salts, stearic acid derivatives, starch, hydrogenated vegetable oils, sodium benzoate, sodium acetate, leucine and magnesium lauryl sulfate.

The present invention also provides a combination of prebiotics and probiotics along with the composition of the present invention which when combined, become synbiotics. The combination of prebiotics and probiotics in the same product as a 1-2 punch has been termed herein synbiotics. This combination of prebiotics and probiotics demonstrate a powerful synergistic effect over the individual prebiotics or probiotics alone. Thus the composition of the present invention may be specifically designed to contain different components which can provide a synbiotic effect.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

References

U.S. Patent Application Publication No. 2009/0087517: Bacterial Growth Enhancer.

U.S. Pat. No. 6,617,126: Method for Improving the Growth and Colorimetric Detection of Bacteria, Yeasts, Fungi or Cocci.

Chan-Blanco, et al., in their publication "Using banana to generate lactic acid through batch process fermentation", APPL MICROBIOL BIOTECHNOL (2003) 63:147-152.

What is claimed is:

1. A method of preparing a plant extract comprising the steps of:
    combining a fruit core from a fruit of a flowering plant, wherein the fruit core is substantially free of: the fruit peel, the fruit ends, and any discoloration, bruises, microbial growth, environmental stress, or any combinations thereof with distilled water, wherein the flowering plant is of the *Musa* genus;
    blending the fruit core and distilled water in a processor to form a smooth mixture;
    separating the blended fruit and distilled water into a supernatant and a sediment, wherein the sediment is discarded;
    sterilizing the supernatant; and
    filtering the sterilized supernatant by tangential flow filtration (TFF) which has a molecular weight cut-off (MWCO) of 500-1000 Daltons to isolate the plant extract which has a molecular weight range of 500-1000 Daltons wherein the plant extract comprises one or more active components responsible for the promotion or enhancement of germination, growth, viability, yield, metabolite production, or any combinations thereof of one or more microorganisms of the genus *Bacillus* when grown in a media comprising the plant extract, wherein the media comprising the plant extract has higher growth promoting activity on the one or more microorganisms of the genus *Bacillus* when compared to a media comprising an extract of the fruit core of a flowering plant of the *Musa* genus that was not subjected to TFF.

2. The method of claim 1, wherein the method further comprises steps of:
    processing the extract with the one or more active components by one or more techniques selected from lyophilization, vacuum centrifugation, spray drying, or any combinations thereof; and
    performing one or more analytical tests or chemical analysis tests on the plant extract, wherein at least one of the test is selected from the group consisting of sugar profile, moisture content, vitamin A analysis, crude protein estimation, complete mineral analysis, non-protein nitrogen (NPN) equivalent to protein, Brix index, specific gravity, vitamin C, crude fiber analysis, pH, fatty acid composition by GC, and any combinations thereof.

3. The method of claim 1, wherein the TFF is a flat sheet or hollow fiber membrane, a tubular membrane, a spiral wound, a hollow fiber, a pressurized, a immersed, or a ceramic filter.

4. The method of claim 1, wherein the one or more microorganisms of the genus *Bacillus* are selected from the group consisting of *Bacillus thuringiensis, Bacillus coagulans, Bacillus subtilis, Bacillus amyloliquefaciens, Bacillus licheniformis*, and any combinations thereof.

5. The method of claim 1, wherein the plant extract is added to a growth, sporulation, or a fermentation medium to promote or enhance spore germination, growth, viability, yield, metabolite production, or any combinations thereof of the one or more microorganisms of the genus *Bacillus*, wherein the growth medium comprises nutrient broth (NB), nutrient agar (NA), Luria-Bertani broth (LB), Mueller-Hinton cation-adjusted broth (MH), a sporulation broth, eosin-methylene blue agar (EMB), yeast and mold (YM), blood agar, MacConkey agar, Hektoen enteric agar (HE), mannitol salt agar (MSA), Terrific Broth (TB), xylose lysine deoxycholate (XLD), RI I-1640 media, molasses-based media, buffered charcoal yeast extract agar, minimal media, or any combinations or modifications thereof.

6. The method of claim 1, wherein the plant extract is added to a growth medium at a concentration ranging from 0.01%-15%, 0.5%-10%, or 1%-5% by volume.

7. The method of claim 1, wherein the fruit is at least one of: (a) ripened and then frozen prior to isolating the fruit core, or (b) the fruit core is isolated and then frozen.

\* \* \* \* \*